(12) United States Patent
Lesch, Jr.

(10) Patent No.: US 6,391,003 B1
(45) Date of Patent: May 21, 2002

(54) LOCKING MECHANISM FOR A JET INJECTOR

(75) Inventor: Paul R. Lesch, Jr., Lexington, MN (US)

(73) Assignee: Antares Pharma, Inc., Minneapolis, MN (US)

(*) Notice: Subject to any disclaimer, the term of this patent is extended or adjusted under 35 U.S.C. 154(b) by 0 days.

(21) Appl. No.: 09/425,965

(22) Filed: Oct. 25, 1999

(51) Int. Cl.[7] .................. A61M 5/00; A61M 5/32
(52) U.S. Cl. ........................ 604/110; 604/198
(58) Field of Search ................... 604/192, 194, 604/195, 196, 197, 198, 110, 68–76, 131, 134, 135, 136, 140–141, 143, 156–157, 181, 187, 207–211; 128/919; 222/34, 35, 309, 298, 295

(56) References Cited

U.S. PATENT DOCUMENTS

| | | | |
|---|---|---|---|
| 3,605,744 A | 9/1971 | Dwyer | 128/218 F |
| 3,702,609 A | 11/1972 | Steiner | 128/218 F |
| 3,797,489 A | 3/1974 | Sarnoff | 128/218 F |
| 3,797,491 A | 3/1974 | Hurschman | 128/218 DA |
| 3,892,237 A | 7/1975 | Steiner | 128/216 |
| 4,127,118 A | 11/1978 | Latorre | 128/79 |
| 4,227,528 A | 10/1980 | Wardlaw | 128/218 F |
| 4,258,713 A | 3/1981 | Wardlaw | 128/218 F |
| 4,282,986 A | 8/1981 | af Ekenstam et al. | 222/1 |
| 4,378,015 A | 3/1983 | Wardlaw | 128/218 F |
| 4,553,962 A | 11/1985 | Brunet | 604/198 |
| 4,719,825 A | 1/1988 | LaHaye et al. | 81/9.22 |
| 4,790,824 A | 12/1988 | Morrow et al. | 604/143 |
| 5,062,830 A | 11/1991 | Dunlap | 604/68 |
| 5,080,648 A | 1/1992 | D'Antonio | 604/72 |
| 5,304,128 A | 4/1994 | Haber et al. | 604/68 |
| 5,318,522 A | 6/1994 | D'Antonio | 604/72 |
| 5,342,308 A * | 8/1994 | Boschetti | |
| 5,391,151 A | 2/1995 | Wilmot et al. | 604/139 |
| 5,505,694 A | 4/1996 | Hubbard et al. | 604/51 |
| 5,540,660 A * | 7/1996 | Jenson | 604/110 |
| 5,562,625 A * | 10/1996 | Stefancin, Jr. | 604/110 |
| 5,562,626 A * | 10/1996 | Sanpietro | 604/110 |
| 5,569,190 A | 10/1996 | D'Antonio | 604/72 |
| 5,599,302 A | 2/1997 | Lilley et al. | 604/68 |
| 5,637,094 A | 6/1997 | Stewart, Jr. et al. | 604/135 |
| 5,769,138 A | 6/1998 | Sadowski et al. | 141/329 |
| 5,951,528 A | 9/1999 | Parkin | 604/239 |
| 6,056,716 A | 5/2000 | D'Antonio et al. | 604/68 |

FOREIGN PATENT DOCUMENTS

| | | |
|---|---|---|
| WO | WO 92/19296 | 11/1992 |
| WO | WO 95/29720 | 11/1995 |
| WO | WO 97/14455 | 4/1997 |
| WO | WO 97/48430 | 12/1997 |
| WO | WO 99/03521 | 1/1999 |
| WO | WO 99/22790 | 5/1999 |
| WO | WO 97/21457 | 6/1999 |

* cited by examiner

Primary Examiner—Brian L. Casler
Assistant Examiner—Catherine Serke
(74) Attorney, Agent, or Firm—Winston & Strawn

(57) ABSTRACT

A needle assisted jet injector having a locking mechanism for reducing the likelihood of inadvertent contact with the needle and deterring intentional reuse of the needle are disclosed. Upon activation of the force generating source, a portion of the needle extends past the nozzle assembly and penetrates the outer layer of skin to deliver the medicament via jet injection to a deeper region. After activation, the needle retracts back into the nozzle assembly. The locking mechanism includes a needle holder and a locking ring, which mate upon activation of the injector and prevent reignition.

21 Claims, 29 Drawing Sheets

LOCKING MECHANISM FOR A JET INJECTOR

FIELD OF THE INVENTION

The present invention is directed to a locking mechanism for use with a device for delivery of medicament, and in particular to a locking mechanism for use with a jet injector equipped with a short needle for reducing the likelihood of inadvertent contact with the needle and deter intentional reuse of die needle.

BACKGROUND OF THE INVENTION

A wide variety of needleless injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin.

As the skin is a tissue composed of several layers and the injector is applied to the external surface of the outermost layer, the delivery pressure must be high enough to penetrate all layers of the skin. The layers of skin include, the epidermis, the outermost layer of skin, the dermis, and the subcutaneous region. The required delivery pressure is typically greater than approximately 4000 p.s.i. (measured as the force of the fluid stream divided by the cross-sectional area of the fluid stream).

Although this pressure is readily achievable with most injectors, there are some circumstances in which delivery of medicament to the subcutaneous region under a reduced pressure is desirable. For example, drugs that require a specific molecular structural arrangement, such as a linear protein configuration, may be rendered ineffective due to shear forces caused by the delivery of the drug at high pressures that alter the structural arrangement of the drug. As it is more difficult to deliver a large volume of fluid at a high pressure compared to a small volume, using a lower pressure facilitates delivery of a larger volume of fluid. Furthermore, the lower pressure could make manufacturing an injector device less expensive. The lower pressure would also reduce adverse stresses on the device and result in a corresponding increased useable device lifetime. Moreover, the lower pressure would make jet injection compatible with medicament stored and delivered in glass ampules, which typically cannot withstand the pressure typically reached by jet injectors.

One of the advantages associated with needleless jet injectors is the absence of a hypodermic needle. Given the aversion to needles possessed by some, the absence of a needle provides a psychological benefit. Even devices that utilize conventional hypodermic needles have attempted to capitalize on this psychological benefit. For example, self-injectors or auto-injectors like the ones disclosed in U.S. Pat. Nos. 4,553,962, 4,378,015 have retractable needles which are hidden until activation. Upon activation, the needle extends from the bottom of the device and penetrates the user's skin to deliver medicament. As none of these devices involves delivery of the medicament using jet injection, the medicament delivery location is limited by the length of the needle. For example, if delivery in the subcutaneous region is desired, the needle must be long enough to reach the subcutaneous region. Furthermore, as auto-injectors operate like syringes, the injection time is several seconds or longer. In contrast, jet injectors typically inject in fractions of a second.

U.S. Pat. No. 5,304,128 to Haber et al. describes a jet injecting syringe that uses a short needle to assist injection. The syringe uses a gas powered driven plunger to force medication through the syringe and out of the needle. The needle is retracted until the syringe is activated and then is extended to puncture the skin of the person injected. However, the needle remains extended after the syringe is used. The extended needle could lead to potential biohazards and safety concerns, such as accidental injections and spreading of diseases. Also, the gas powered plunger is both complicated and expensive to manufacture.

PCT Publication No. WO 99/03521 of Novo Nordisk discloses an undefined concept of "jet" injection. However, this publication does not teach one the details of the driving mechanism necessary to practice the concept.

PCT Publication No. WO 99/22790 of Elan Corporation teaches a needle assisted injector having a retractable shield that conceals the needle both before and after use of the injector. The disclosed injector has a driving mechanism that operates on pressure created by a chemical reaction. Because of this chemically operated driving mechanism, the injecting time for the injector is at least three seconds and more likely greater than five seconds. This relatively long injection time may create discomfort in the patient receiving the injection. Also, the needle may move during the lengthy injection and add to the patients discomfort.

Even with minimally invasive medical procedures, it is advantageous to maintain the time for the procedures at a minimum. Thus, there exists a need for a needle assisted jet injector that operates at relatively low pressure and that is capable of quickly delivering medicament. There also exists a need for such an injector having a retractable or concealed needle to prevent the medical hazards associated with exposed needles. There is also a need for an injector having a retractable or concealable needle which is usable only once so that, after use, the needle is prevented from subsequent use until removed and replaced.

SUMMARY OF THE INVENTION

The present invention relates to a locking mechanism for use with a needle assisted jet injector. The needle assisted jet injector has a needle assembly with a needle and a needle guard associated with the needle assembly. The needle guard is for placement against a surface to be injected and for guarding the needle before and after an injection of the injector. The needle guard is movable between a first retracted position wherein the needle is retracted inside the needle guard, an extended position wherein the needle extends outside the needle guard for injection into the surface, and a second retracted position wherein the needle is retracted inside the needle guard after injection.

The locking mechanism includes a holder member and locking means. The holder member is configured and dimensioned to hold the needle assembly and has at least one first engaging portion. The locking member is operatively associated with the needle guard and the holder member. The locking means is preferably provided in the form of a locking member that has at least one second engaging portion for engagement with the at least one first engaging portion of the holder member in the extended and second retracted positions. The locking member is associated with the needle guard in the first retracted position, is associated with the holder member in the extended and second retracted positions, and is in blocking relation with the needle guard in the second retracted position so as to block further movement of the needle guard into the extended position and deter reuse of the needle.

The locking member may include a substantially annular portion and at least one outwardly-biased leg extending from a distal end of the annular portion. In this embodiment, the needle guard includes at least one pocket for accepting the at least one leg when the locking member is associated with the needle guard in the first retracted position. The leg maintains its position in association with the needle guard due to its outwardly-biased force and is resilient such that it is removable from the at least one needle guard pocket upon the application of sufficient force to overcome the outwardly biased force of the leg.

The second engaging portion of the locking member may include an undercut portion formed at a proximal end of the annular portion of the locking member. The undercut portion is preferably dimensioned and configured to accept the first engaging portion of the holder member for mating therewith. The proximal end of the annular portion may also include a ramp portion on an inner surface extending inwardly from the end thereof. The locking member ramp portion is angled relative to an outer circumferential surface of the annular portion for engagement with the first engaging portion of the holder member before the holder member engages the undercut portion.

The outwardly biased leg of the locking member preferably springs outwardly after disengagement with the needle guard pocket. These legs then abut a shoulder formed on an inner surface of the needle guard in the second retracted position to prevent reuse of the needle by substantially blocking proximal movement of the needle guard.

The holder member may include a substantially cylindrical portion at a proximal end thereof, the at least one first engaging portion at a distal end thereof, and an inner wall positioned substantially therebetween. The cylindrical portion and inner wall are configured and dimensioned for mating with the needle assembly.

The inner wall of the holder member may include a circular opening extending between the proximal and distal sides thereof for receiving a portion of the needle assembly therethrough. The first engaging portion of the holder member is at least one arm extending distally from the inner wall. The arm preferably includes an extension portion configured and dimensioned for seating in the second engaging portion of the locking member. The extension portion of the arm may also include a ramped portion for association with the locking member. The ramped portion of the holder member may preferably be complementary to the ramped portion of the locking member such that both ramped portions allow the other ramped portion to slide thereupon allowing the first engaging portion to engage the second engaging portion in the extended position.

BRIEF DESCRIPTION OF THE DRAWINGS

FIG. 14b is a cross-sectional view of the needle assisted jet injector of FIG. 14a taken along a plane perpendicular to that of FIG. 14a;

FIG. 18b is a cross-sectional view of the latch assembly of FIGS. 14a and 14b taken along line A—A of FIG. 18a;

FIG. 22b is a cross-sectional view of the needle guard of FIG. 22a;

DESCRIPTION OF THE PREFERRED EMBODIMENTS

Figure 1:
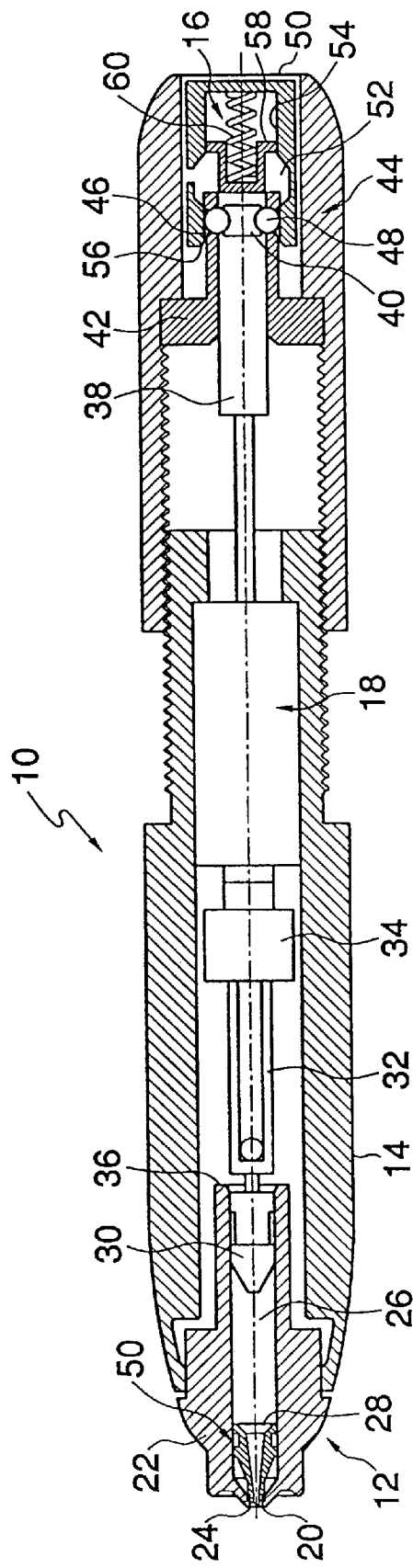
FIG. 1 is a cross-sectional view of a needle assisted jet injector according to the present invention.

For convenience, the same or equivalent elements of the invention of embodiments illustrated in the drawings have been identified with the same reference numerals. Further, in the description that follows, any reference to either orientation or direction is intended primarily for the convenience of description and is not intended in any way to limit the scope of the present invention thereto.

As shown in FIG. 1, a jet injector 10 according to the present invention comprises a nozzle assembly 12 attached to a housing 14. As used in this application, the term distal shall designate the end or direction toward the front of jet injector 10. The term proximal shall designate the end or direction toward the rear of the injector. The term longitudinal designates an axis connecting nozzle assembly 12 to jet injector 10, and the term transverse designates a direction substantially perpendicular to the longitudinal direction including arcs along the surface of jet injector 10, or nozzle assembly 12.

Nozzle assembly 12 can be threadably connected to housing 14 such that it can be readily attached and detached. Alternatively, other known structures for mounting or attaching two components can be utilized as well to detachably mate nozzle assembly 12 to housing 14. In this manner, injector 10 can be reused with various nozzle assemblies that may contain different medications of different doses either together or at different times. For instance, nozzle assembly 12 can be prefilled with medication and disposed of after each use. Further, a medication filling device such as a coupling device can be used to fill the fluid chamber with medication. U.S. Pat. No. 5,769,138 to Sadowski et al., the disclosure of which is herein incorporated by reference, is directed to such a coupling device.

A trigger assembly 16 is located at the proximal end of housing 14. Trigger assembly 16 activates and triggers an energy source or force generating means 18 which forces medicament out of nozzle assembly 12. Energy source 18 can be a coil spring, a gas spring, or a gas propellant.

According to a first embodiment of the present invention, nozzle assembly 12 has an injection assisting needle 20 movable within nozzle assembly 12. Needle 20 will be discussed in detail after first describing the other components of injector 10. The nozzle assembly 12 includes a nozzle member 22 having an opening 24 at the distal end, preferably having a diameter of about 0.04–0.4 inches or any other suitable diameter that would allow for the introduction of injection assisting needle 20 therein. Nozzle member 22 includes a cylindrical fluid chamber 26 terminating at the distal end in a right circular cone 28. Cone 28 can be a convex cone (as shown), a right circular cone, or any outer suitable configuration. A plunger 30 having a pressure wall contoured to cone 28 is positioned to slide within fluid chamber 26. Plunger 30 can include sealing means such as one or more O-rings or the like (not shown) that are formed around its outer periphery to provide a seal, or the plunger itself can be a seal, as described in U.S. Pat. No. 5,062,830, the disclosure of which is incorporated herein by reference. The plunger can also include additional sealing means at spaced intervals to provide a better seal.

Plunger 30 is connected to a ram 32 which in turn is connected to energy source 18. Alternatively, ram 32 can be integrally formed with an energy mechanism if desired. An inertia mass 34 is connected to or integrally formed with ram 32 near the end of ram 32 closest to plunger 30. Inertia mass 34 can be removably connected to ram 32 such that the mass can be adjusted to accommodate different types of injections, taking into consideration, for instance, the viscosity of the medication, the initial pressure build up desired, the strength of energy source 18, and the depth of injection penetration, etc. Inertia mass 34 cooperates with ram retainer 36 to limit the distance that ram 32 can travel toward nozzle assembly 12. One important safety aspect of this feature is that ram 32 cannot become a dangerous projectile if injector 10 is fired when nozzle assembly 12 is not present.

Trigger assembly 16 includes a trigger extension 38 having a trigger engaging notch 40. Trigger extension 38 is attached to the end of ram 32, for example, by a threaded engagement. Trigger assembly 16 also comprises a latch housing sleeve 42 fixedly attached to an actuating mechanism 44. Actuating mechanism 44 is shown as a threaded coupling that operates by rotation movement. Latch housing sleeve 42 has a throughbore dimensioned to allow passage of trigger extension 38. Latch housing sleeve 42 further has a plurality of sidewall openings 46 dimensioned to allow passage of balls or ball bearings 48. A tubular button 50 having one open end and a closed end is telescopingly positioned with latch housing sleeve 42 as shown. Button 50 has a circumferential or annular groove 52 formed on an inner wall 54 thereof to allow portions of the balls 48 to engage groove 52 when trigger assembly 16 is in the fired position, i.e., not engaged with trigger extension 38 (not shown). Balls 48 are positioned so that they are substantially flush with an inner side wall surface 56 of latch housing sleeve 42 to allow trigger extension 38 to pass through latch housing sleeve 42. A latch ball retaining cup 58 is telescopingly positioned within button 50. A compression spring 60 is positioned between the cup 58 and button 50 to bias button 50 and cup 58 away from each other in the axial direction.

Figure 2:
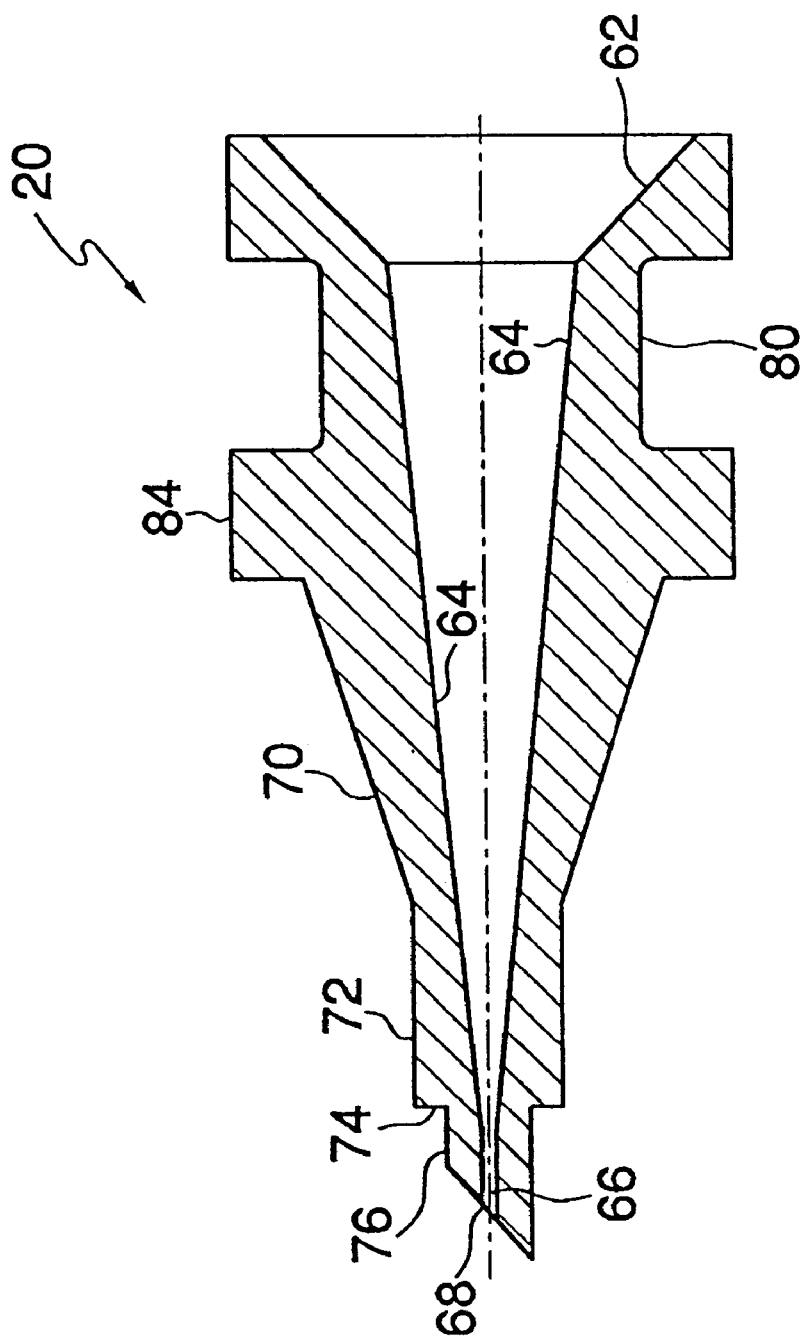
FIG. 2 is a cross-sectional view of the needle on the jet injector of FIG. 1.
Figure 3:
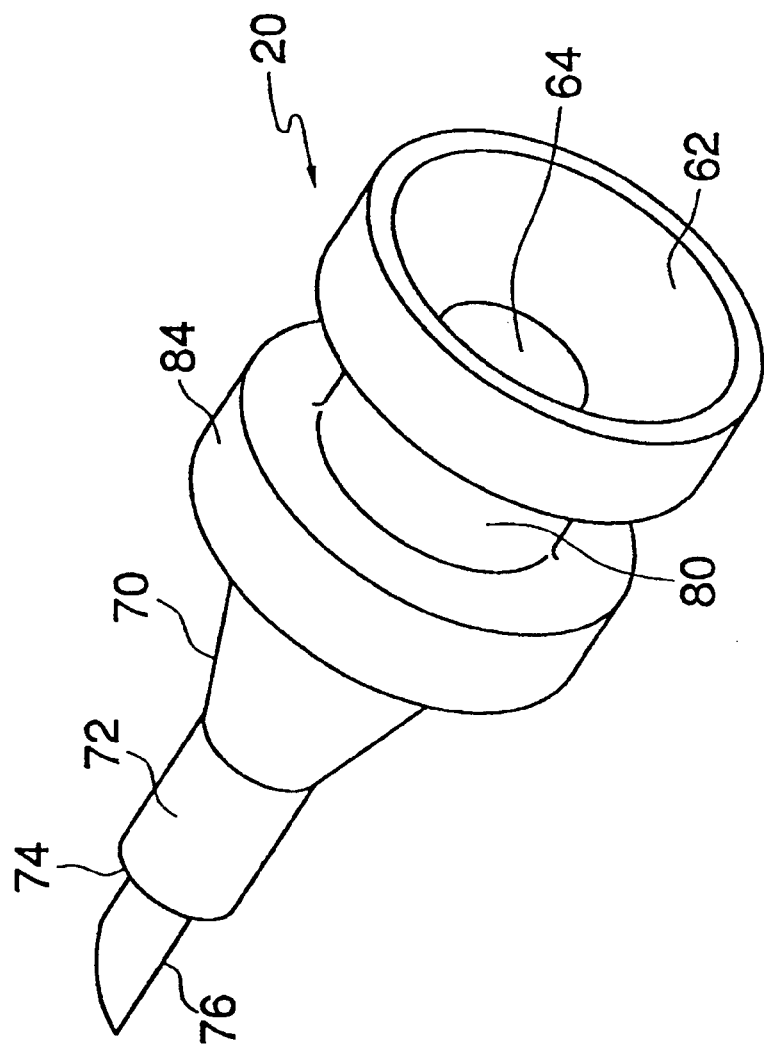
FIG. 3 is a perspective view of the needle of FIG. 2.

The structure of injection assisting needle 20 is best seen in FIGS. 2 and 3. Needle 20 has a plunger receptor 62 at the proximal end which is configured to accommodate plunger 30 as it slides within fluid chamber 26. Although plunger receptor 62 can be of any shape conforming to the exterior profile of plunger 30, it is preferably conical. A needle inner wall 64 is contoured to narrow like a funnel to a needle discharge channel 66 to accelerate the fluid as it is discharged. Needle discharge channel 66 extends to a discharge orifice 68 at the distal end of needle 20. Needle discharge orifice 68 has a diameter of 0.004 to 0.012 inches. Preferably, the diameter is 0.005 to 0.0075 inches.

The outer periphery of needle 20 can be of varied geometries such that it fits within fluid chamber 26 of nozzle assembly 12. Advantageously, needle 20 has a conical body section 70 which narrows gradually or tapers towards a cylindrical body section 72 of smaller circumference. Preferably, a shoulder 74 is positioned to separate a needle tip 76 from cylindrical body section 72. Needle tip 76 is also cylindrical, but has a smaller circumference than cylindrical body section 72 such that needle tip 76 can fit within and extend through opening 24 of nozzle assembly 12. However, cylindrical body section 72 of needle 20 has a circumference such that shoulder section 74, existing at the transition between cylindrical body section 72 and needle tip 76, prevents cylindrical body section 72 from existing within opening 24. The length of needle tip 76 from its end to shoulder 74 is approximately 1 to 5 mm. Thus, needle tip 76 will penetrate the skin to a depth less than 5 mm. It should also be noted that although needle tip 76 is shown having a single beveled end at a 45° angle, needle tip 76 can have any shape that penetrates the skin.

Figure 4:
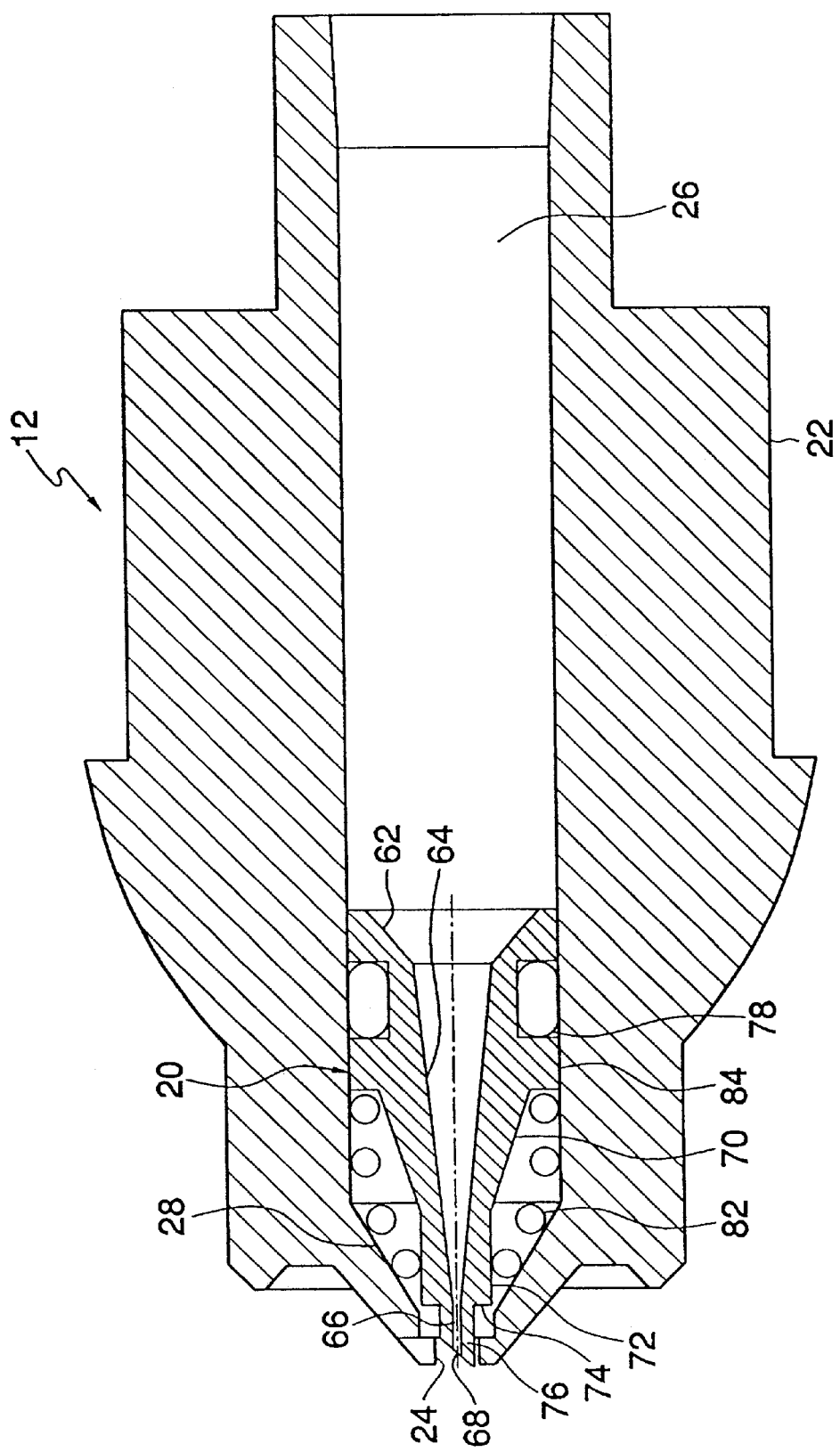
FIG. 4 is an enlarged cross-sectional view of the jet injector of FIG. 1 with the needle in the retracted position.
Figure 5:
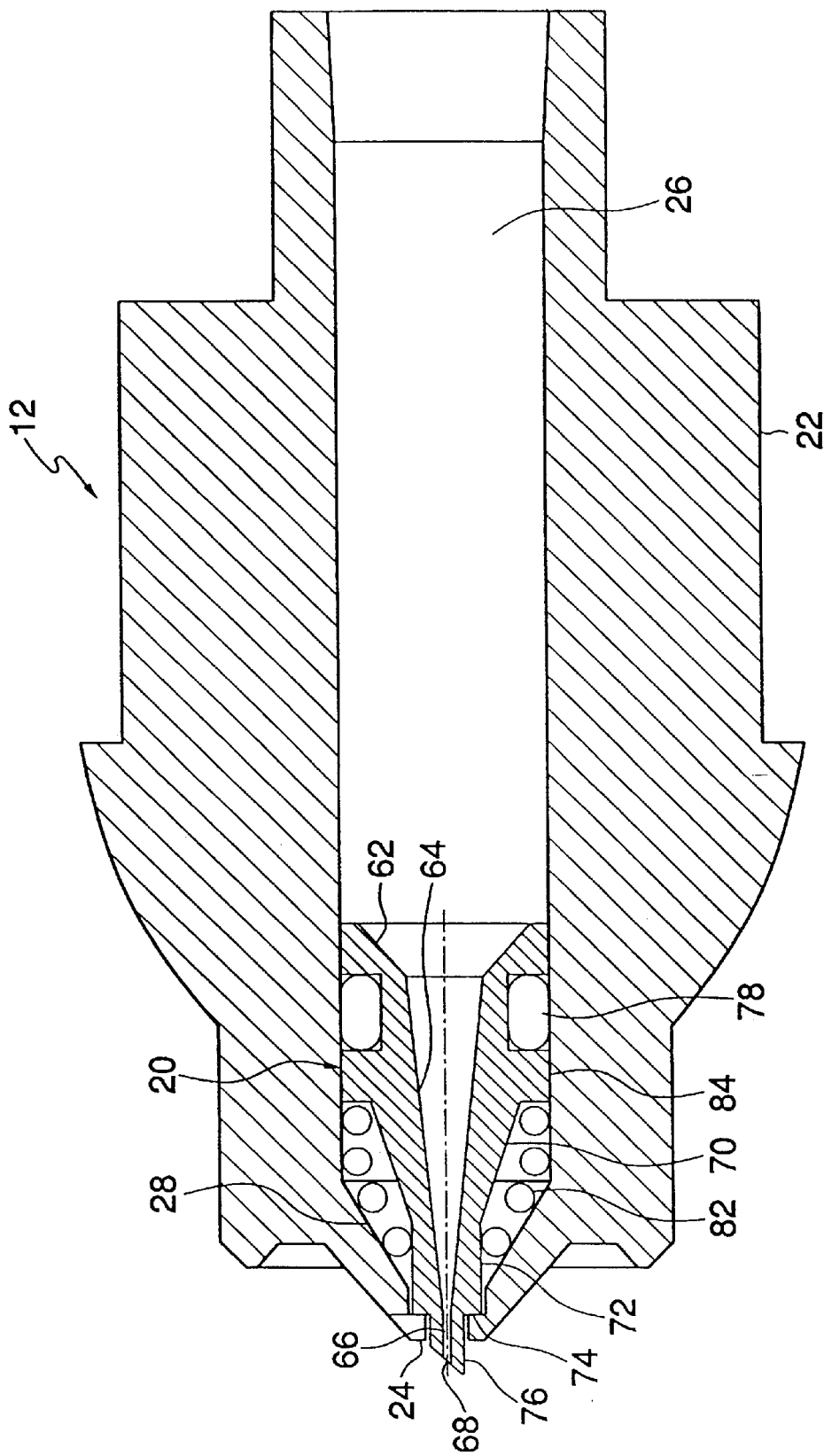
FIG. 5 is an enlarged cross-sectional view of the jet injector of FIG. 1 with the needle in the extended position.

As shown in FIGS. 4 and 5, needle 20 is positioned coaxially and retractably within the distal end of fluid chamber 26 such that when injector 10 is fired, needle tip 76 extends out opening 24 of nozzle assembly 12 at a speed sufficient to penetrate the outer layer of skin. By inserting needle tip 76 to a depth less than 5 mm, typically only the epidermis of the skin is penetrated and the pressure needed to deliver the medicament to the desired region by jet injection is lower than that would otherwise be needed with needleless jet injection. While delivery of medicament by syringes and auto-injectors is limited by the length of the needle, the needle assisted jet injector according to the present invention delivers the medicament to a depth deeper than the length of the needle. This depth can include any region of the skin and beyond including intradermal, subcutaneous, and intramuscular.

To provide a seal between needle 20 and fluid chamber 26, needle 20 includes a sealing means such as an O-ring 78 or the like formed around the outer periphery of needle 20 and accommodated by slot 80. In an alternative embodiment shown in FIG. 6, needle 120 itself is the seal. Thus, slot 80 is not needed. Needle 120 also differs from needle 20 in that cylindrical body section 72 is absent so that conical body section 70 terminates at shoulder 74.

FIG. 5 illustrates injection assisting needle 20 in its extended position. Needle tip 76 extends beyond the distal end of nozzle assembly 12. Shoulder 74 abuts the bored out inner section of nozzle opening 24 to prevent needle 20 from extending beyond needle tip 76. A retraction element 82, in this embodiment a spring, is compressed to provide a recoil force once the medicament is expelled so that needle tip 76 will retract back into nozzle opening 24. Needle 20 preferably has a ridge 84, the distal surface of which provides an annular area for the compression of retraction element 82. Alternatively, a washer can be used instead of the ridge 84 to contain O-ring 78 and compress the retracting mechanism during operation.

Figure 6:
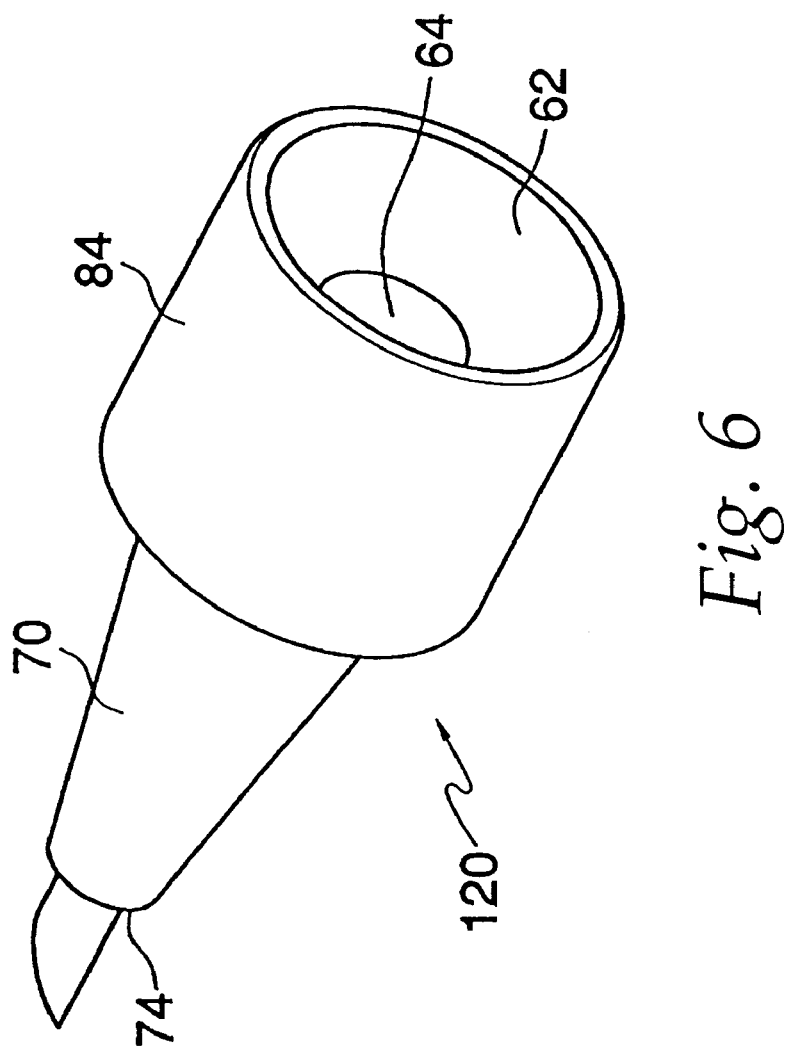
FIG. 6 is a perspective view of a second embodiment of the needle according to the present invention.
Figure 7:
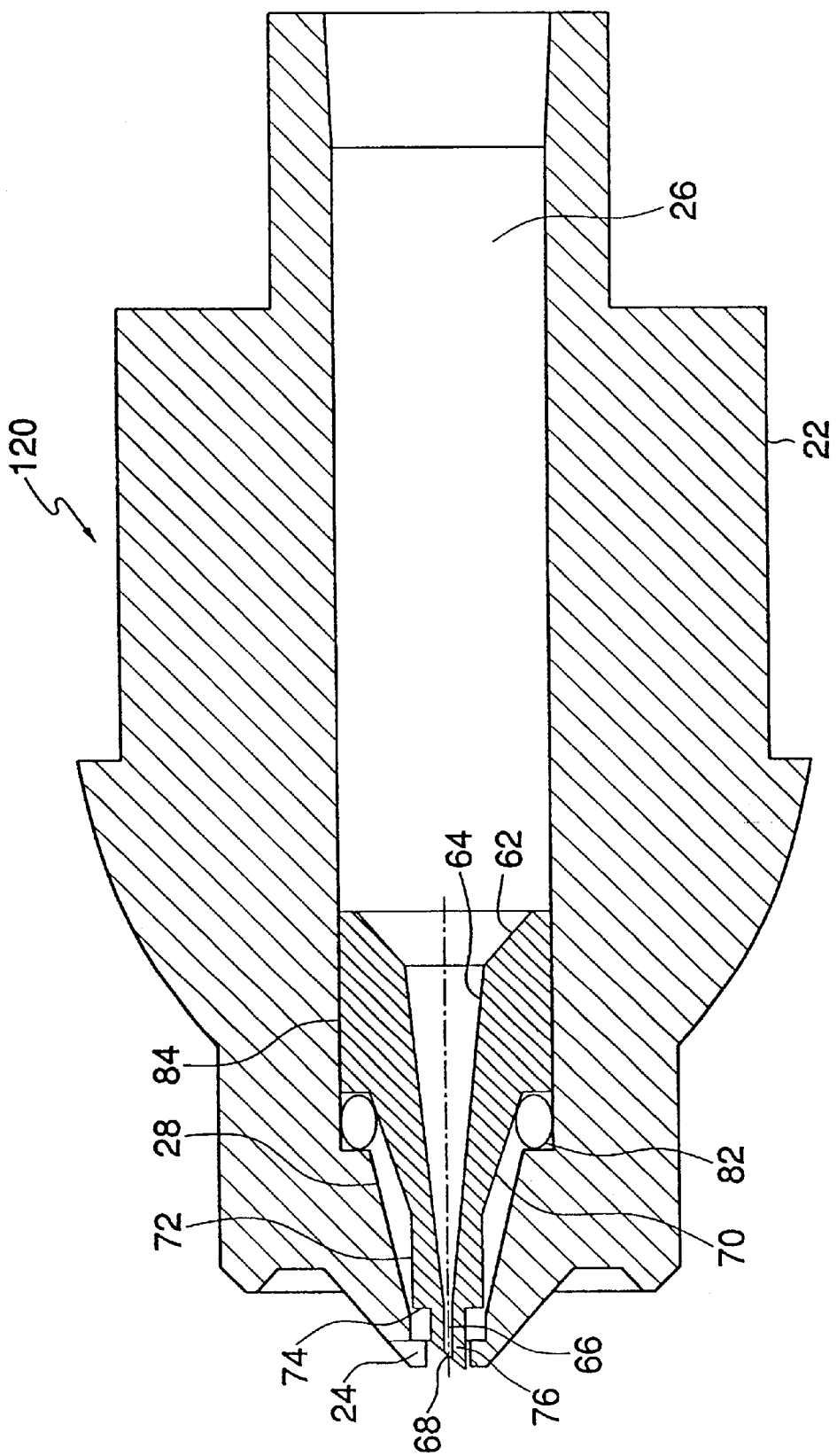
FIG. 7 is a partial cross-sectional view of a jet injector according to the present invention with the needle of FIG. 6 in the retracted position.
Figure 8:
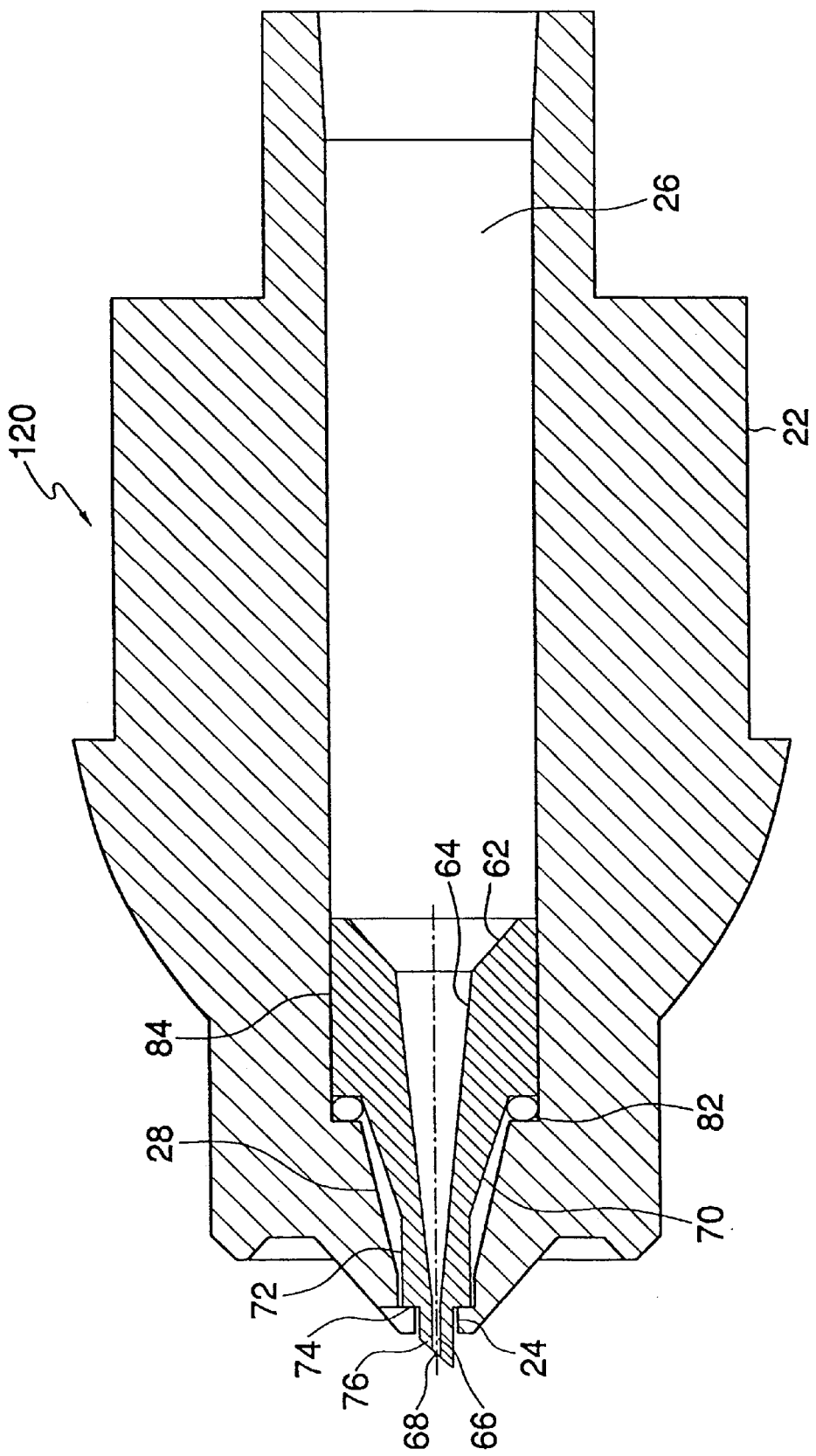
FIG. 8 is a partial cross-sectional view of a jet injector according to the present invention with the needle of FIG. 6 in the extended position.

FIGS. 7 and 8 show needle 120 of FIG. 6 with nozzle assembly 12 in which retraction element 82 is a resilient O-ring or other like material known to those skilled in the art. When an O-ring is used as retraction element 82, it can also act as a sealing mechanism, and for this reason the O-ring is preferred. The interior of needle 120 is similar to that of needle 20. FIG. 7 illustrates needle 120 in the retracted condition, before expelling medicament, and FIG. 8 shows the extended condition during which medicament is expelled. Similar to embodiments previously described, this embodiment functions to extend the needle tip 76 beyond nozzle opening 24 and penetrate the outer layer of the patient's skin during operation. Also, similar to embodiments previously described, needle 120 also preferably has a ridge 84 around the proximal end to provide a surface which compresses the resilient material when the injector is triggered.

Figure 9:
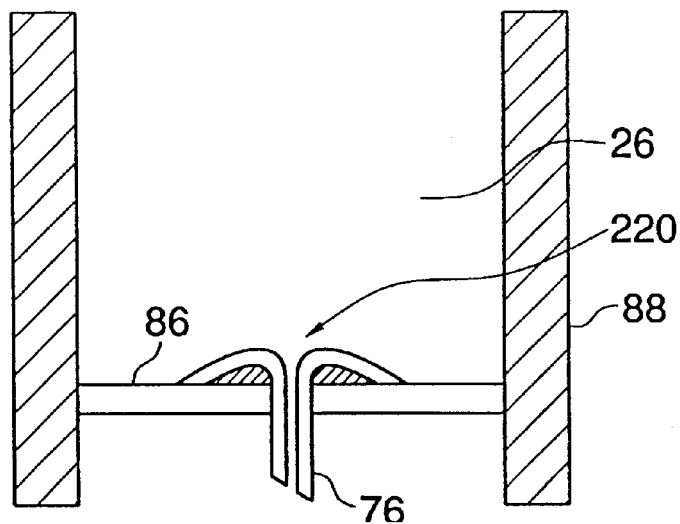
FIG. 9 is a cross-sectional view of another embodiment of the present invention with a flexible member as the retraction element and the needle in the retracted position.
Figure 10:
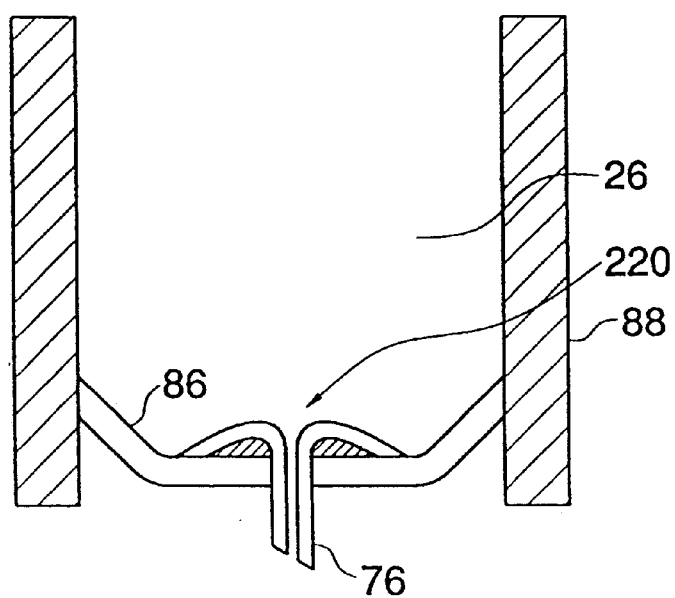
FIG. 10 is a cross-sectional view of the embodiment of FIG. 9 with the needle in the extended position.

Another embodiment of the present invention, shown in FIGS. 9 and 10, uses a flexible member 86 as the retraction element. FIG. 9 illustrates the neutral condition before expelling the medicament. Flexible membrane 86 spans between walls 88 of nozzle assembly 12 which define fluid chamber 26 for holding medicament. Similar to embodiments previously described, the distal end of nozzle walls 88 act to conceal needle tip 76 until the injector is fired. Needle 220 is attached to flexible membrane 86 by any conventional means known to those skilled in the art. Preferably, needle 220 is integrally attached to flexible membrane 86 with an adhesive. FIG. 10 shows needle 220 in its extended position where the needle tip 76 extends beyond the end of walls 88 such that needle tip 76 penetrates the outer layer of skin to allow injection and deliver of the medicine at reduced pressure.

Other embodiments of the present invention relate to injectors with a fixed needle, i.e. a non-retracting needle that permanently extends beyond the nozzle assembly. Both a one-piece and a two-piece nozzle assembly with a fixed needle can be used and are contemplated by this invention.

Figure 11:
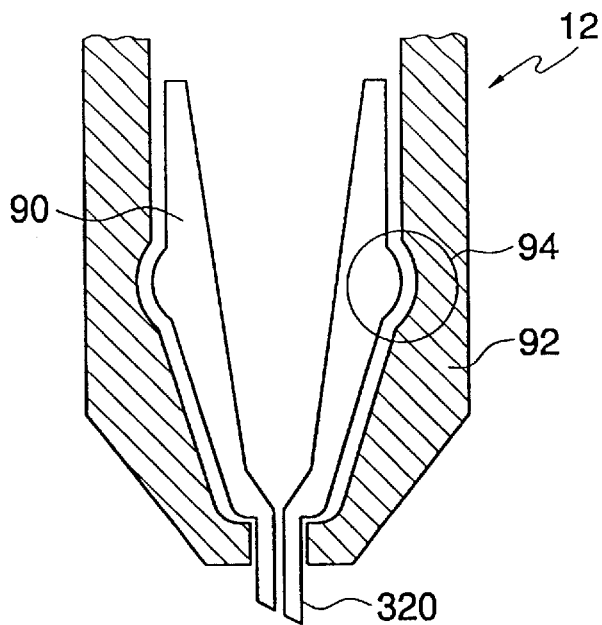
FIG. 11 is a cross-sectional view of a two piece nozzle assembly having a fixed needle.
Figure 12:
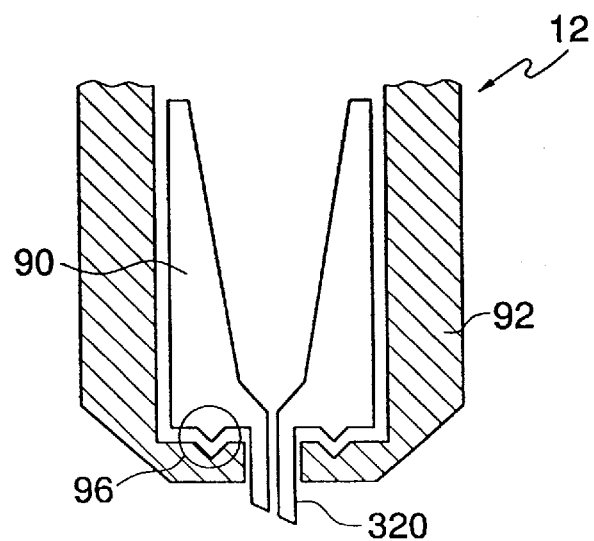
FIG. 12 is a cross-sectional view of another embodiment of a two piece nozzle assembly having a fixed needle.

FIGS. 11 and 12 show embodiments of the present invention with a two piece nozzle assembly with a fixed needle 320. A first section 90 of nozzle assembly 12 has needle 320 at the distal end and can either be attached internally or externally to a second section 92 to form nozzle assembly member 12. Although any conventional attaching means can be used, such as solvent or adhesive bonding, FIG. 11 shows a preferable friction-fining or snapping attaching means 94 for both internal and external attachment of first section 90 and second section 92. FIG. 12 shows a preferable ultrasonic bonding means 96 of attachment. Although ultrasonic bonding features 96 can be placed at any location to attach the two pieces, preferably, the ultrasonic bonding features 96 are along the distal end at the interface between first and second sections 90, 92 to facilitate ease of manufacturing.

Figure 13:
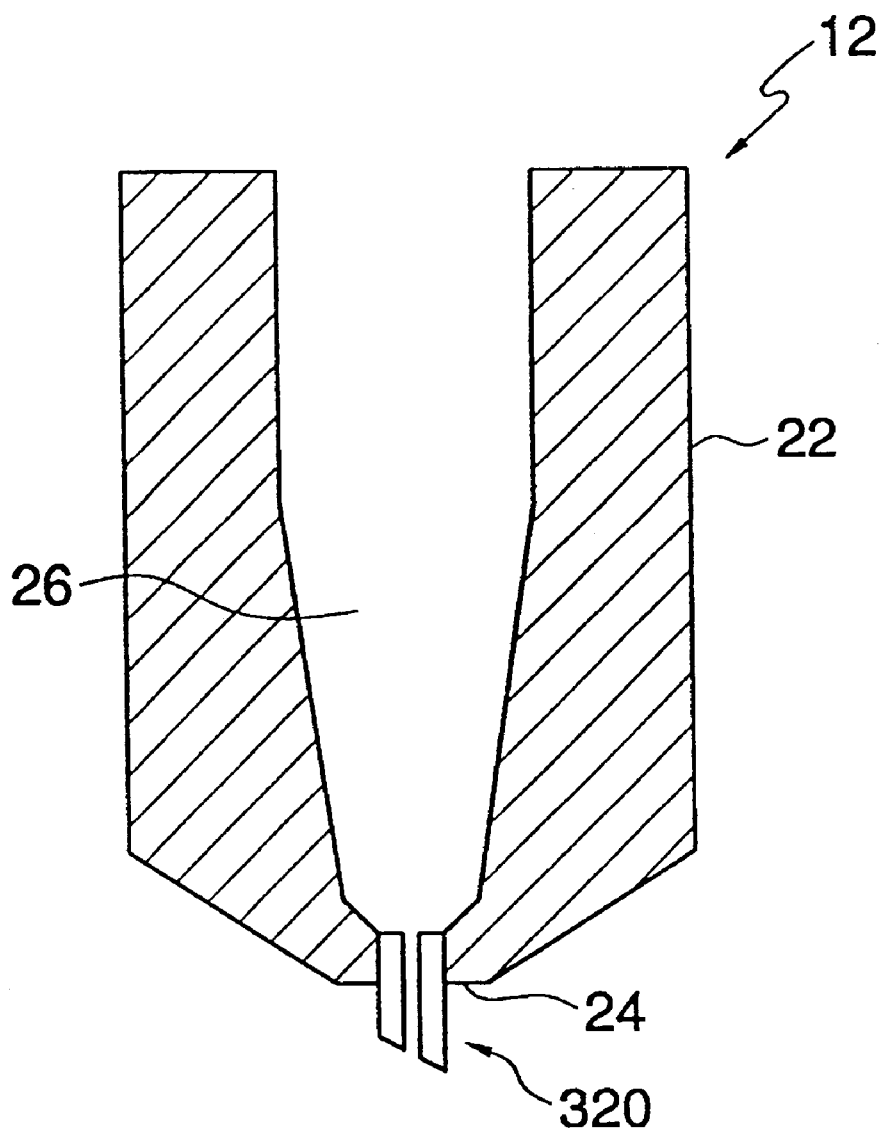
FIG. 13 is a cross-sectional view of another embodiment of a two piece nozzle assembly having a fixed needle.

Another embodiment of a multi-piece nozzle assembly with fixed needle 320 is shown in FIG. 13. The nozzle assembly consists of nozzle member 22 having an opening 24 designed to receive a tubular insert to create fixed needle 320. Although FIG. 13 shows a multi-piece nozzle assembly, fixed needle 320 can be made to be integral with nozzle assembly 12.

Figure 14A:
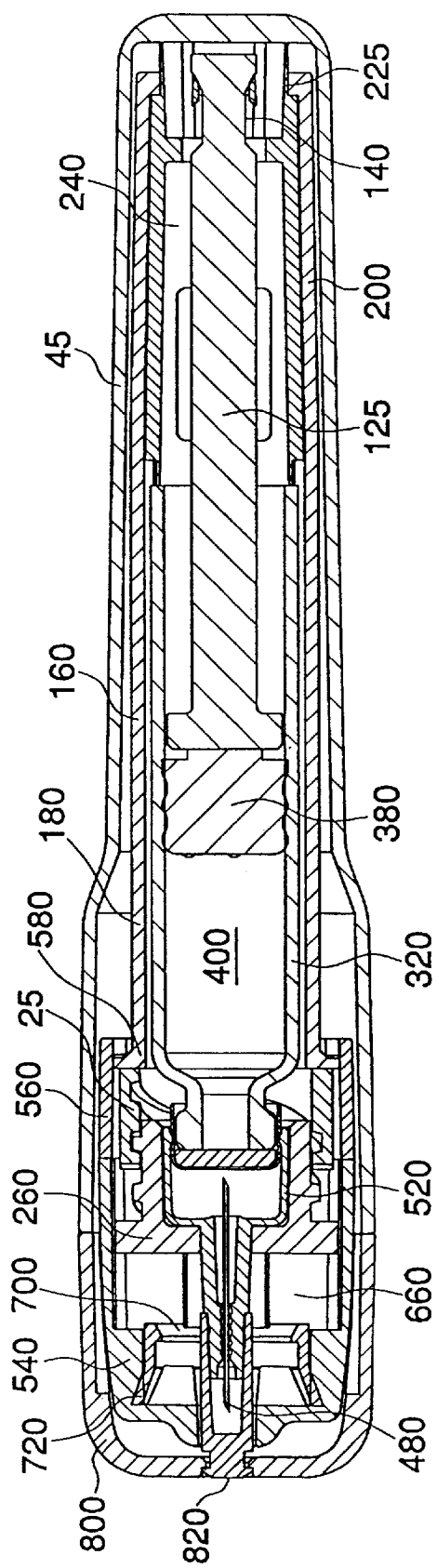
FIG. 14a is a cross-sectional view of a needle assisted jet injector according to a preferred embodiment of the present invention.
Figure 14B:
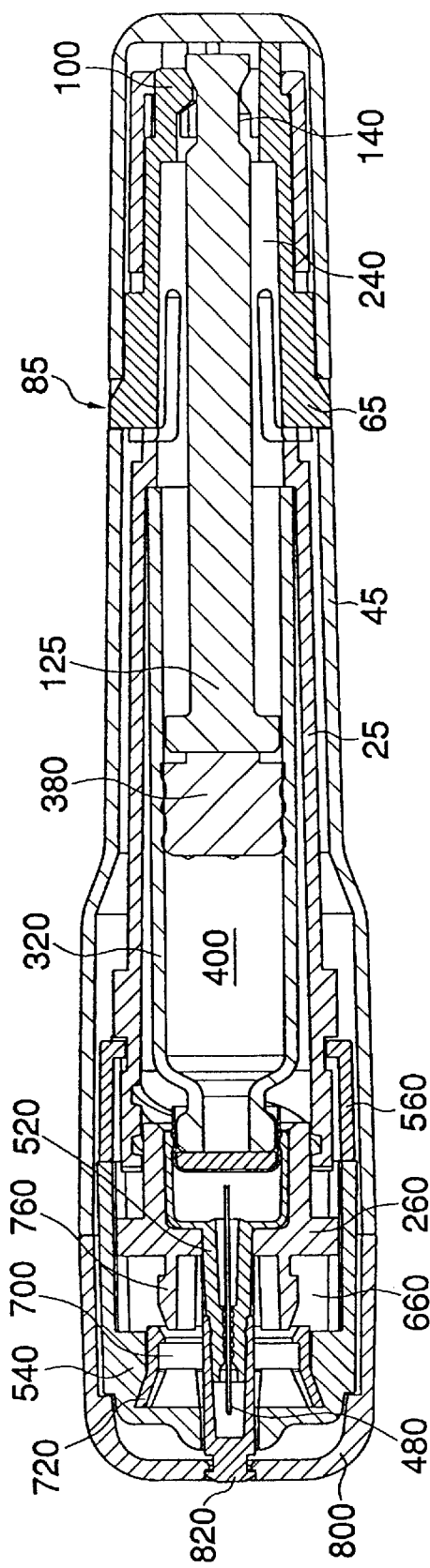
Figure 15:
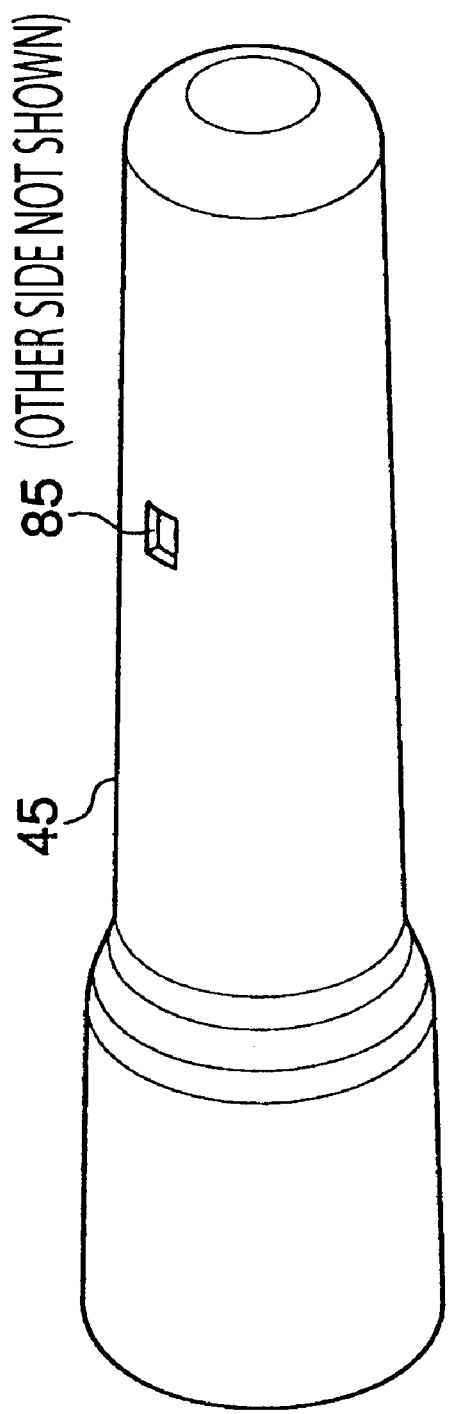
FIG. 15 is a perspective view of the outer housing of the needle assisted jet injector of FIGS. 14a and 14b.
Figure 16:
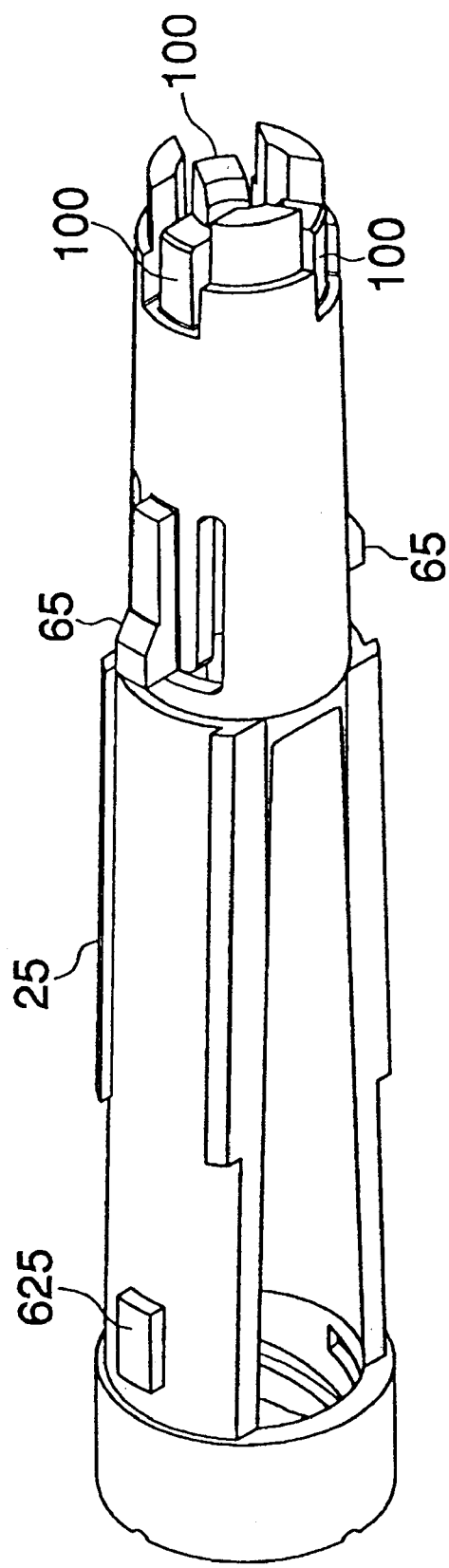
FIG. 16 is a perspective view of the inner housing of the injector of FIGS. 14a and 14b.

FIG. 14a and FIG. 14b depict a preferred embodiment of the present invention having a retractable shield around the needle. An inner housing 25, shown in FIG. 16, snaps inside an outer housing 45, using a pair of snaps 65 located on the inner housing 25. The snaps 65 protrude through openings 85 in the outer housing 45, shown in FIG. 15, and maintain the inner housing 25 and the outer housing 45 in a fixed relationship with one another. Other techniques known in the art, such as gluing and welding, could be used to hold the inner housing 25 and outer housing 45 together.

Figure 17:
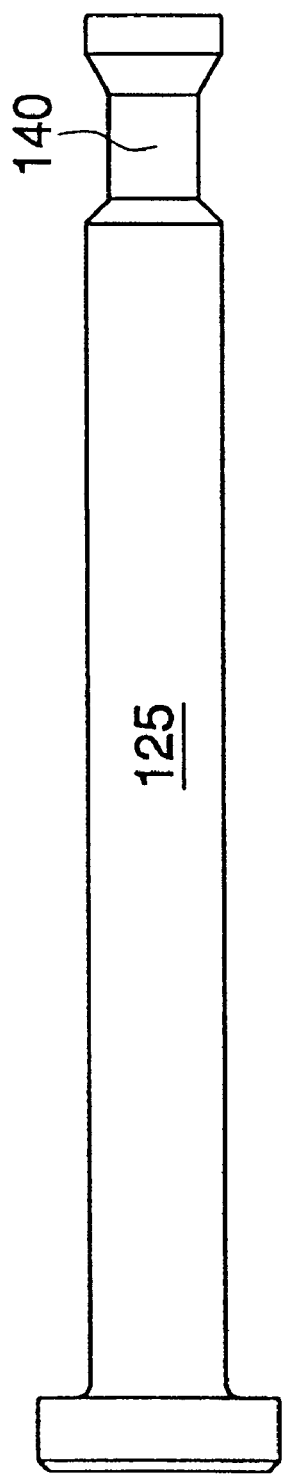
FIG. 17 is an elevational view of the ram of the injector of FIGS. 14a and 14b.
Figure 18A:
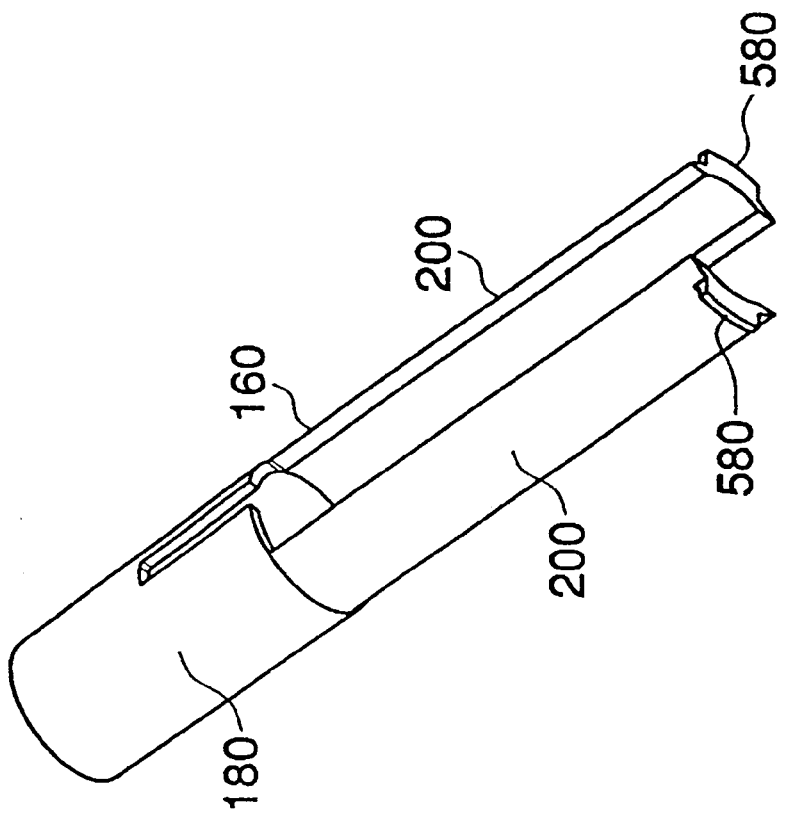
FIG. 18a is perspective view of the latch assembly of FIGS. 14a and 14b.
Figure 18B:
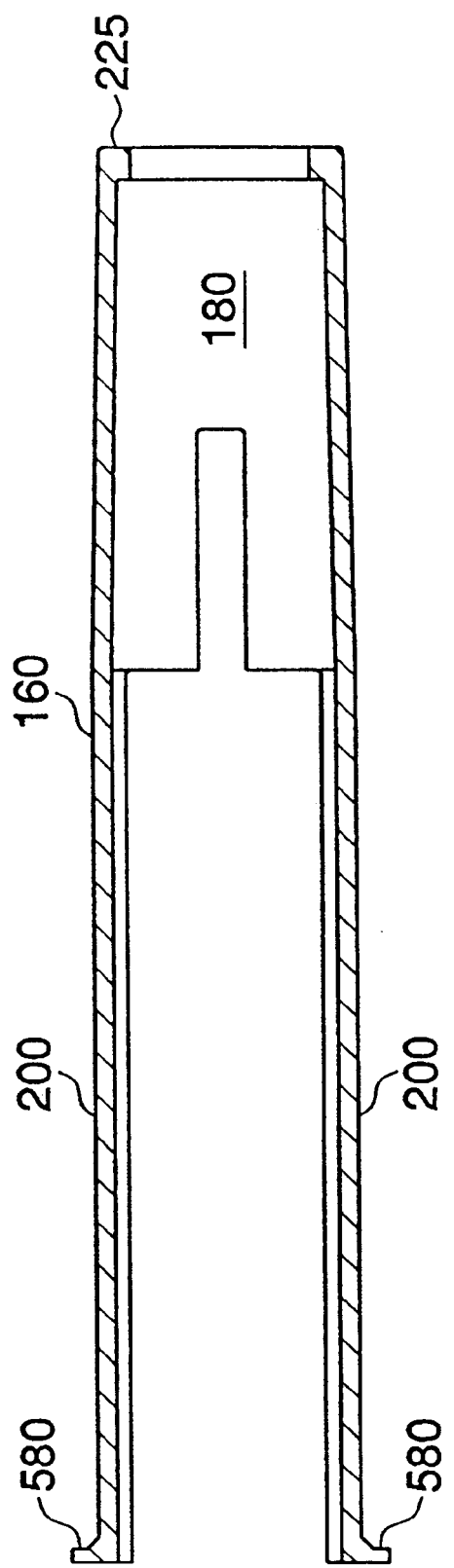

The inner housing 25 has three trigger protrusions 100 extending from its distal end. These trigger protrusions 100 are shaped to mate with an annular recess 140 in ram 125 (FIG. 17). Ram 125 is urged toward the distal end of the injector with a compression spring 240, however other energizing devices capable of producing an injection of up to 2 ml in about 2.5 seconds or less could be used. These energizing sources typically include rubber elastomers and compressed gas cartridges. A latch 160, shown in FIG. 18a, is slidable inside the outer housing 45 and surrounds the inner housing 25. The latch 160 has a barrel portion 180 at its distal end and a pair of extensions 200 at its proximal end. When the jet injector is ready to be fired, ridge 225 on the barrel portion 180, shown in FIG. 18b, contacts the trigger protrusions 100 and maintains them in the annular recess 140 in ram 125, preventing the ram 125 from firing under the force of compression spring 240.

Figure 19:
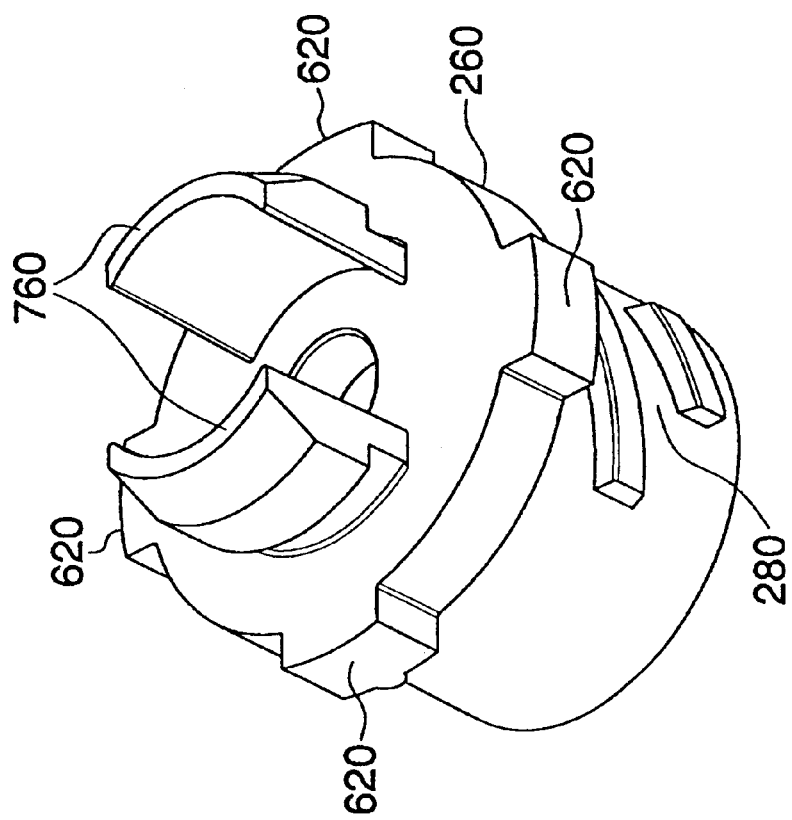
FIG. 19 is a perspective view of the needle holder of FIGS. 14a and 14b.
Figure 20A:
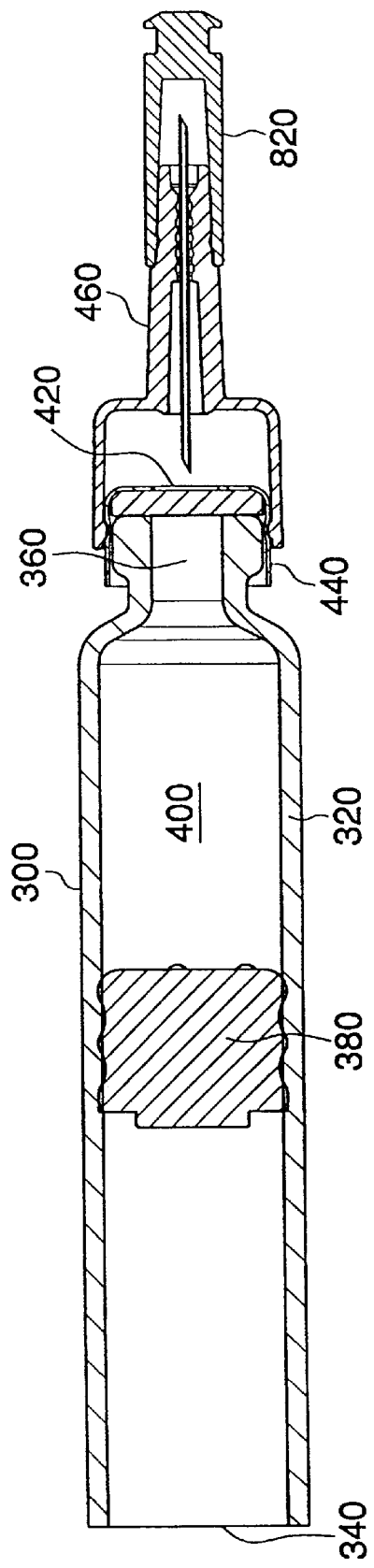
FIG. 20a is a cross-sectional view of the cartridge assembly of FIGS. 14a and 14b.
Figure 32:
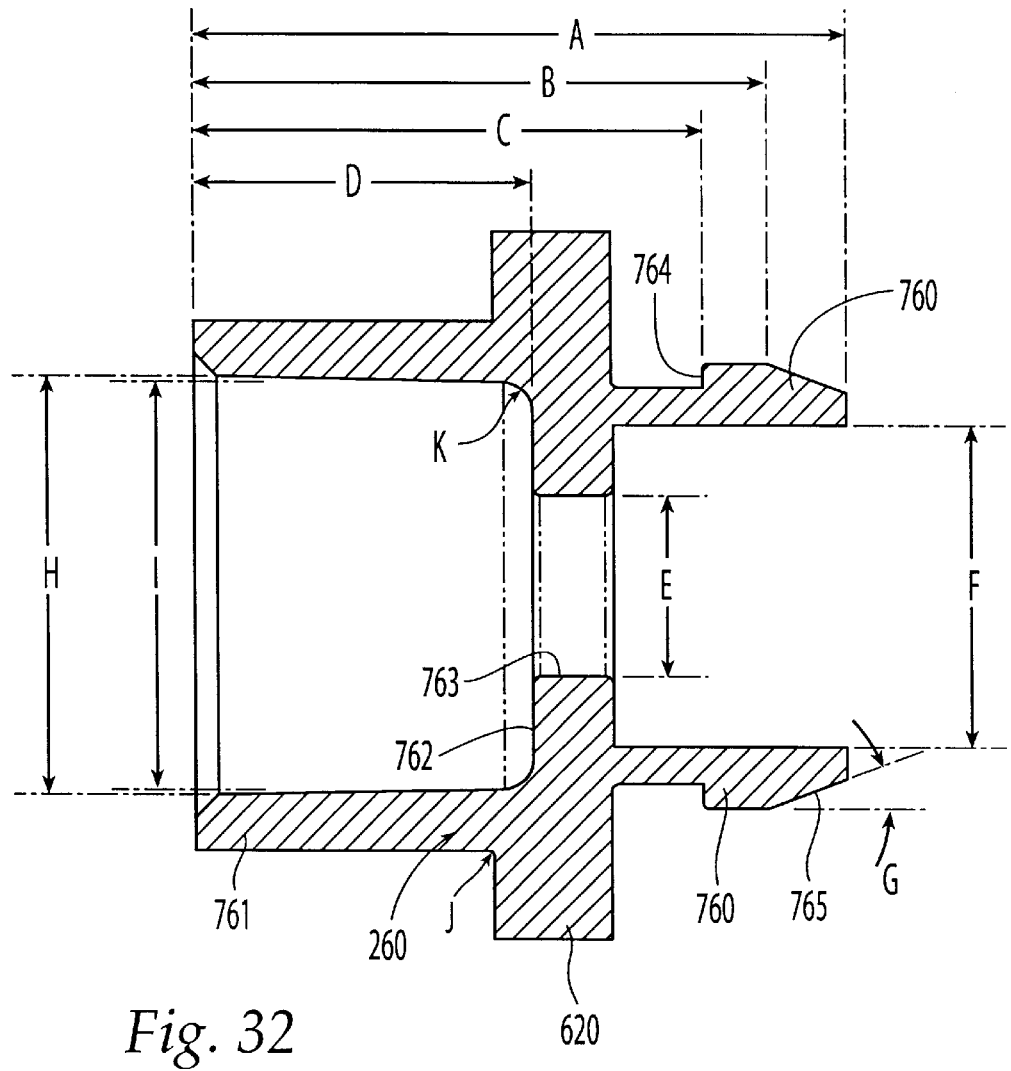
FIG. 32 is a cross-sectional view of the needle holder of FIG. 28.

A needle holder 260, shown in FIGS. 19 and 32, mounts onto the inner housing 25 with right hand threads 280 and holds a cartridge assembly 300 inside the inner housing 25. As best shown in FIG. 20a, the cartridge assembly 300 consists of a glass ampule 320 having an opening 340 in its proximal end and a seal 360 on its distal end. The glass ampule 320 typically holds between 0.02 and 2 mL of a medicament 400. Instead of glass, the ampule 320 can also be constructed of metal or other suitable materials known in the art. A rubber stopper 380 is slideable within the glass ampule 320 and seals the opening 340 in its proximal end of the glass ampule 320 so the medicament 400 stays inside the glass ampule 320. The seal 360 on the distal end comprises a rubber seal 420 formed on the end of the ampule 320 by conventional techniques, such as an aluminum cap 440 having a hole in its end. The ram 125 extends into the opening 340 in the proximal end of the glass ampule 320 and abuts the rubber stopper 380. To provide a visual indication of the device's status, at least a portion of the outer housing 45 is constructed of transparent or translucent material, so that the cartridge assembly 300 can be viewed by the user.

Figure 21A:
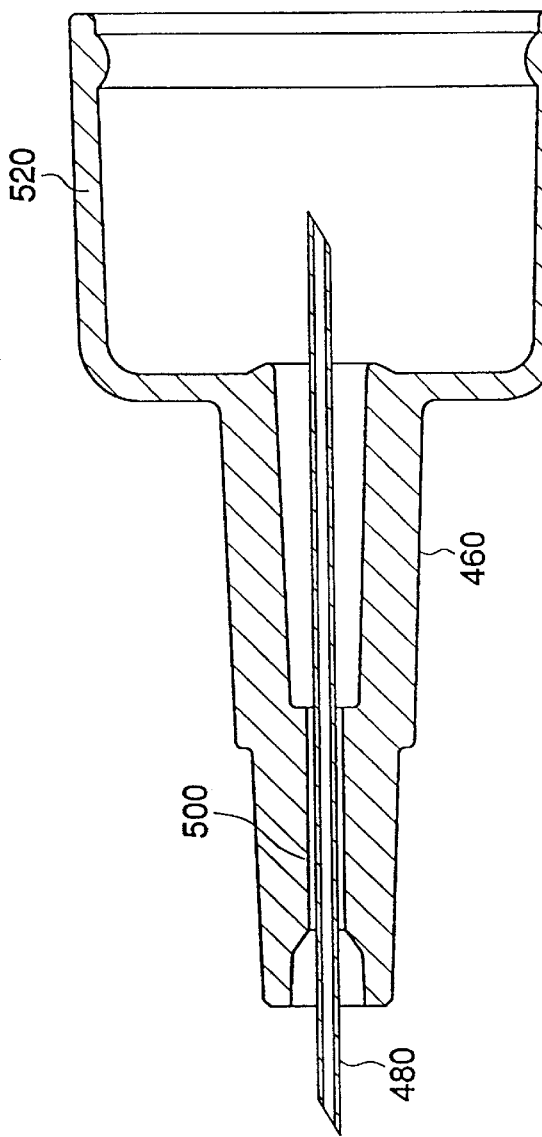
FIG. 21a is a cross-sectional view of the needle assembly of FIGS. 14a and 14b.

A needle assembly 460, shown in FIG. 21, consists of an injecting needle 480 glued inside a longitudinal pocket 500 in the needle hub 520. Grooves or other surface treatment on the longitudinal pocket 500 and on the injecting needle 480 enhance bonding between the injecting needle 480 and the needle hub 520. Alternatively, other known methods of fixing, such as molding, may be used to secure the injecting needle 480 to the needle hub 520.

Figure 21B:
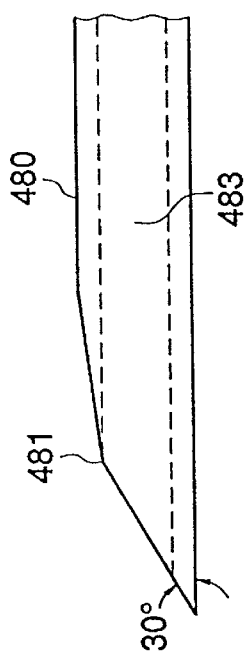
FIG. 21b is a cross-sectional view of the injecting needle of FIGS. 14a and 14b.

To allow for an appropriate injection time, the injecting needle 480 is of 27 gauge, however other gauges may be suitable for different applications. The length of the needle 480 that extends beyond the distal end of the needle hub 520, and is used for injection, is preferably between 1 and 5. As shown in FIG. 21b, the injecting needle 480 preferably has a 30° point. This angle decreases the length of the bevel 481 and thereby increases the effective length of the lumen 483. The increase in the effective length of the lumen 483 reduces the percentage of incomplete injections.

Needle assembly 460 is mounted to the needle holder 260, and clockwise rotation of the needle holder 260 approximately one quarter of a turn threads it further into the inner housing 25 and forces the proximal end of the injecting needle 480 through rubber seal 420, thereby creating the drug path.

Figure 22A:
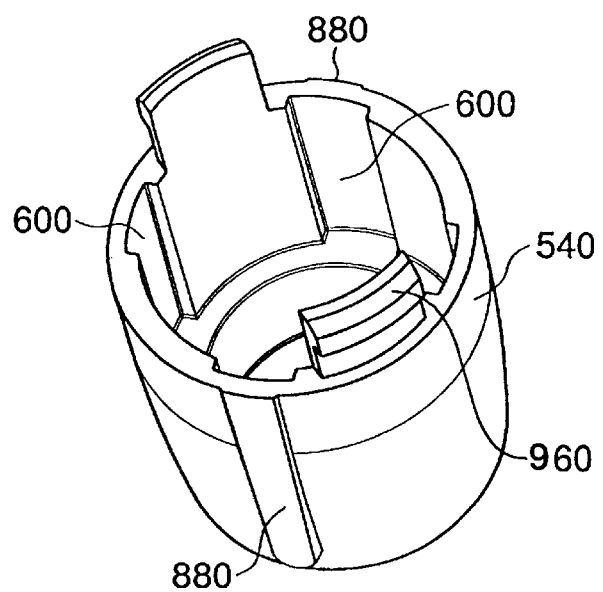
FIG. 22a is a perspective view of the needle guard of FIGS. 14a and 14b.
Figure 23A:
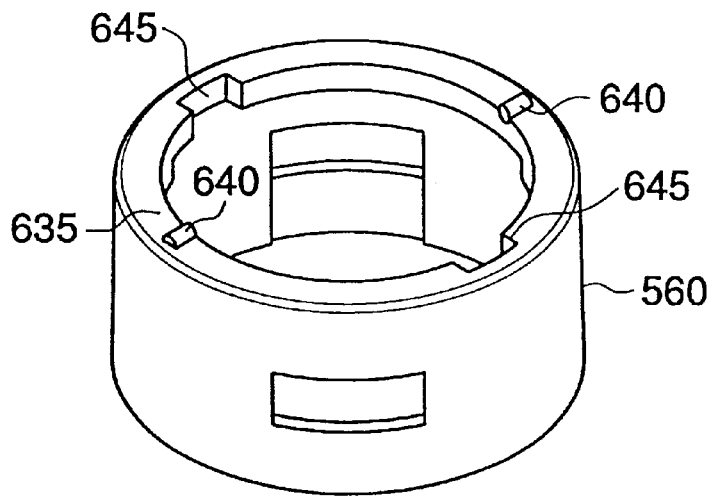
FIG. 23a is a first perspective view of the needle guard cap of FIGS. 14a and 14b.
Figure 23B:
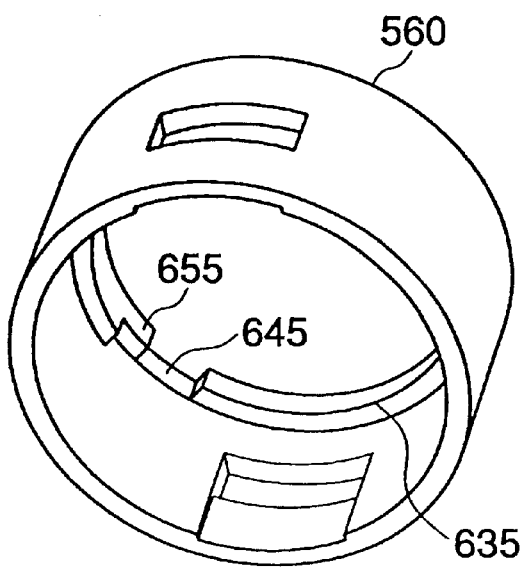
FIG. 23b is a second perspective view of the needle guard cap of FIGS. 14a and 14b.

A needle guard 540, depicted in FIG. 22a, is located at the distal end of the injecting device and conceals the injecting needle 480. The needle guard 540 snaps together with the needle guard cap 560, which is shown in FIGS. 23a and 23b. The needle guard cap 560 slides on extensions 200 of the latch 160, thereby allowing the needle guard 540 to slide longitudinally on the distal end of the injector to expose the injecting needle 480. Feet 580 at the end of extensions 200 prevent the needle guard cap 560 and consequently the needle guard 540 from sliding completely off the end of the device.

Recesses 600 in the needle guard 540 and corresponding bosses 620 on the needle holder 260 translate any rotation of the needle guard 540 into rotation of the needle holder 260. Abutments 655 on the inner surface of the needle guard cap 560, shown in FIG. 23b, are positioned relative to the feet 580 of the latch 160 to inhibit counter-clockwise rotation of the needle holder 260. This prevents the user from unscrewing the device and removing the cartridge assembly 300 from it.

The needle guard cap has a inner flange 635 with a pair of cutouts 645 therein. The cutouts 645 correspond to the pair of bosses 625 on the inner housing 25. The flange 635 acts to prevent motion of the needle guard cap 560 and the needle guard 540 toward the proximal end of the device unless the cutouts 645 are rotated into alignment with the pair of bosses 625. This acts as a safety feature to prevent accidental firing of the injector. Alternatively, other known mechanisms, such as a removable safety strip can be used to prevent accidental firing of the injector.

A return spring 660 (not shown) rests on the needle holder 260 and urges the needle guard 540 toward the distal end of the injector, thereby keeping the injecting needle 480 concealed. A pair of stops 640, shown in FIG. 23, extend from the needle guard cap 560 and are positioned relative to bosses 625 on the inner housing 25 such that the needle guard 540 and needle holder 260 cannot rotate clockwise under the force of return spring 660.

Pressing the needle guard 540 toward the proximal end of the device causes the needle guard cap 560 to push the latch 160 longitudinally toward the proximal end of the device, thereby moving the ridge 225 on the barrel portion 180 of the latch 160 off the trigger protrusions 100 on the inner housing 25. This allows the trigger protrusions 100 to flex out of the annular recess 140 in the ram 125, thereby causing the ram 125 to fire under the force of compression spring 240. When the ram 125 fires, it slides rubber stopper 380 in the glass ampule 320 toward the distal end of the device, causing the medicament 400 to flow through the drug path (created by turning the needle holder 260 clockwise one quarter turn prior to firing, as discussed above) and eject from the injecting needle 480.

Figure 22B:
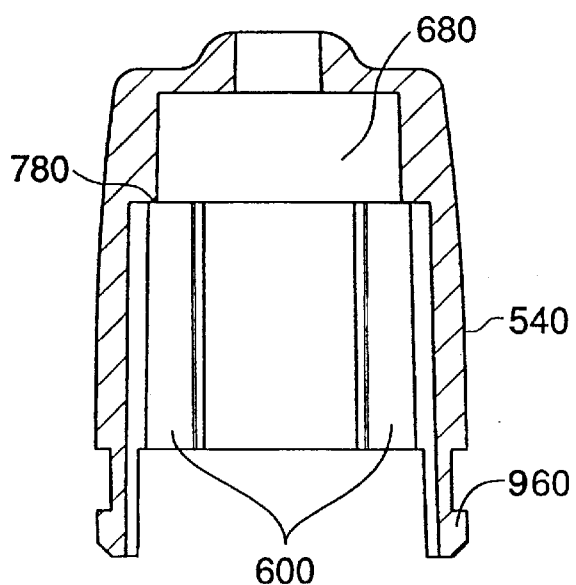
Figure 24:
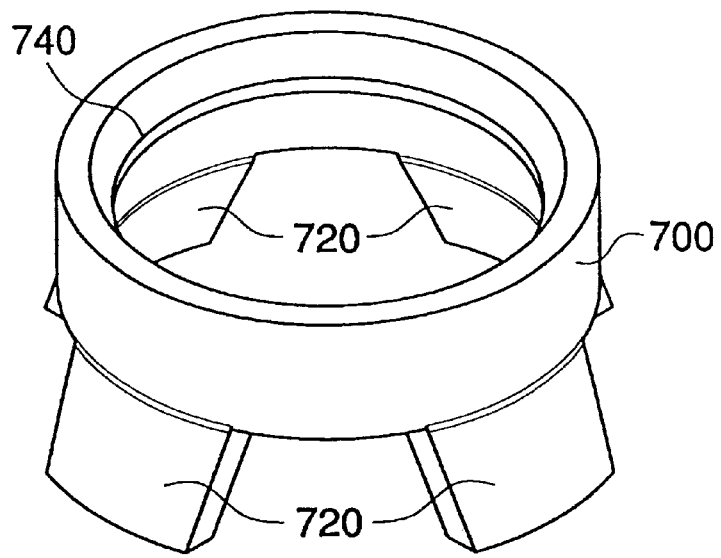
FIG. 24 is a perspective view of the locking ring of FIGS. 14a and 14b.
Figure 31:
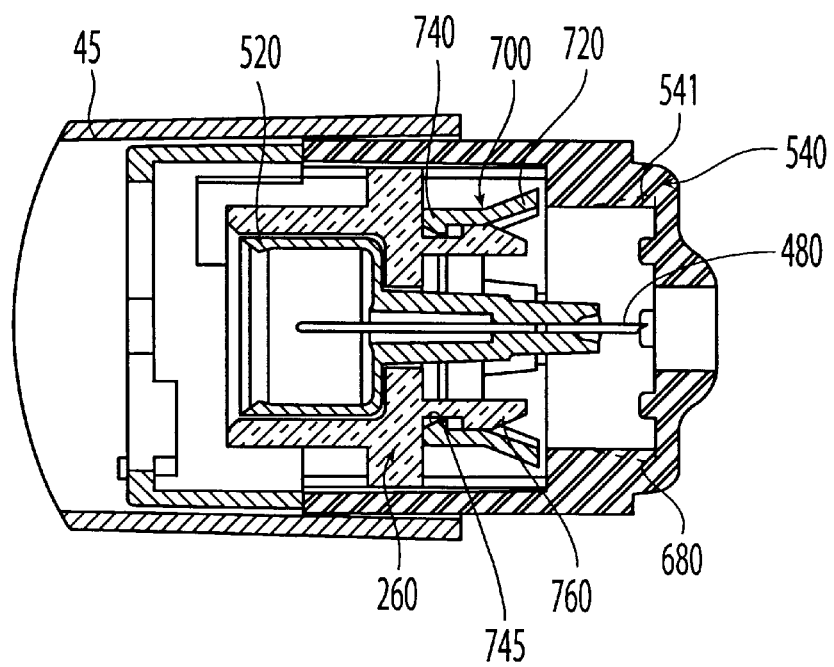
FIG. 31 is a cross-sectional view of the jet injector of FIG. 28 with the needle in a retracted position after use and locked into an inoperative position.

As depicted in FIG. 22b, needle guard 540 has a pocket 680 located therein. Locking means, in the specific form of a locking ring 700, shown in FIG. 24, sits in pocket 680 and prevents re-exposure of the injecting needle 480 after the device has been fired. As shown in FIG. 31, locking ring 700 has splayed legs 720 at a first end and an undercut 740 at a second end that mates with extensions 960, shown in FIG. 22a, which protrude from the needle holder 260. As shown in FIG. 31, locking ring 700 includes ramp portion 745 at the second end for engagement which similarly configured ramp portions 765 on extensions 760 of the needle holder 260. Ramp portions 745 and 765 provide for ease of mating between extensions 760 of the needle holder 260 and undercut 740 of the locking ring 700. Upon depression of the needle guard 540 toward the proximal end of the device, extensions 760 engage the undercut 740 and become locked thereon. When the needle guard 540 returns to its original position, the locking ring 700 is pulled from pocket 680 in the needle guard 540 and splayed legs 720 expand radially outward. Upon an attempt to re-depress the needle guard 540, splayed legs 720 catch shoulder 780 on the needle guard 540 and restrict further movement of the needle guard 540, thereby preventing re-exposure of the injecting needle 480.

Referring to FIG. 32, a preferred embodiment of needle holder 260 is depicted. Needle holder 260 includes extensions 760 with ramped portions 765 at a distal end and a cylindrical wall portion 761 at the proximal end. An inner wall 762 is provided between the distal and proximal ends of the needle holder and includes a circular opening 763 for receiving the needle assembly 520. Inner wall 762 is preferably arranged substantially perpendicular to cylindrical wall portion 761. Needle hub 520 seats fittingly inside the cylindrical wall portion 761 of the needle holder 260 and needle assembly 520 extends through opening 763 so that needle 480 extends out beyond extensions 760. Extensions 760 extend axially and distally outward from inner wall 762. Bosses 620 extend transversely outwardly from inner wall 762 in approximately the same plane as inner wall 762. Bosses 620 also extend transversely outwardly from cylindrical wall portion 761 such that bosses 620 are the outermost portions of needle holder 260.

In one embodiment of the needle holder 260 shown in FIG. 32, needle holder 260 has a length A of about 0.62 inches. Ramped portion 765 is preferably at an angle G of approximately 20°. The ramped portion is approximately 0.08 inches in length such that dimension B is approximately 0.539 inches. Extensions 760 include shoulder 764 for engaging undercut 740 of locking ring 700 such that dimension C is approximately 0.48inches. Cylindrical wall portion 761 is preferably 0.32 inches in length D and is associated with inner wall 762 via an inner radiused curve K, having an approximate radius of 0.025inches. Cylindrical wall portion 762 is associated with bosses 620 via an outer radiused curved portion J, having an approximate radius of 0.005 inches. Cylindrical wall portion 761 is preferably tapered outwardly such that the outer diameter opening H is greater than the inner diameter opening I. In one embodiment outer diameter opening H is approximately 0.39 inches and inner diameter opening is approximately 0.381 inches. In this embodiment, circular opening 763 of inner wall 762 has a diameter E of approximately 0.17 inches and the distance F between extensions 760 is approximately 0.3 inches.

Figure 33:
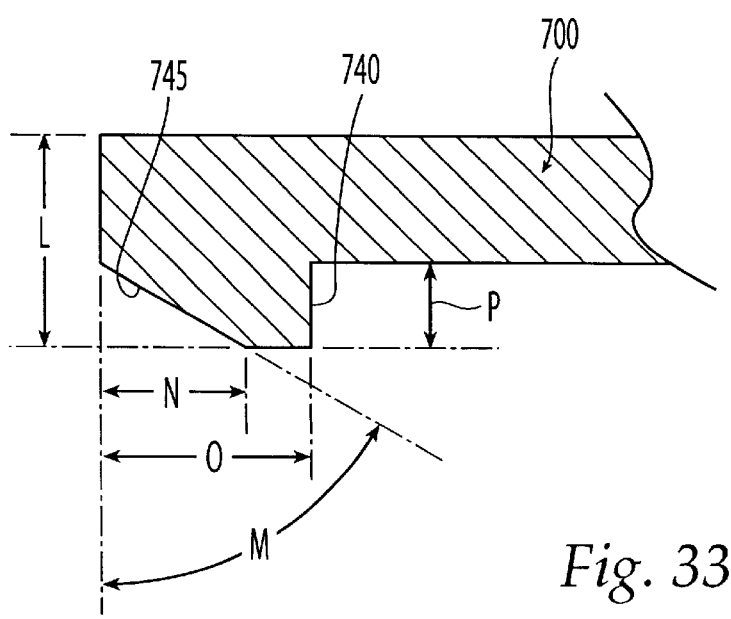
FIG. 33 is a cross-sectional view of the prongs on the locking ring of FIG. 28.

Referring now to FIG. 33, the proximal end of locking ring 700 is shown as including undercut 740 and ramped portion 745. In one embodiment of the locking ring 700, ramped portion 745 is preferably at an angle M of approximately 60° and is approximately 0.035 inches in length N. Undercut 740 is formed inwardly a distance O of approximately 0.05 inches relative to the proximal end of locking ring 700. Locking ring 700 is approximately 0.05 inches in thickness L and undercut 740 extends transversely a distance P of approximately 0.02 inches. Ramp 745 is configured and dimensioned for engaging ramped portion 765 of needle holder 260.

While several dimensions are provided in FIGS. 32 and 33 for the proximal end of locking ring 700 and for the needle holder 260, they are purely exemplary in nature. It will be understood that other dimensions will also be useful and functional, the invention not being so limited in scope.

Figure 25:
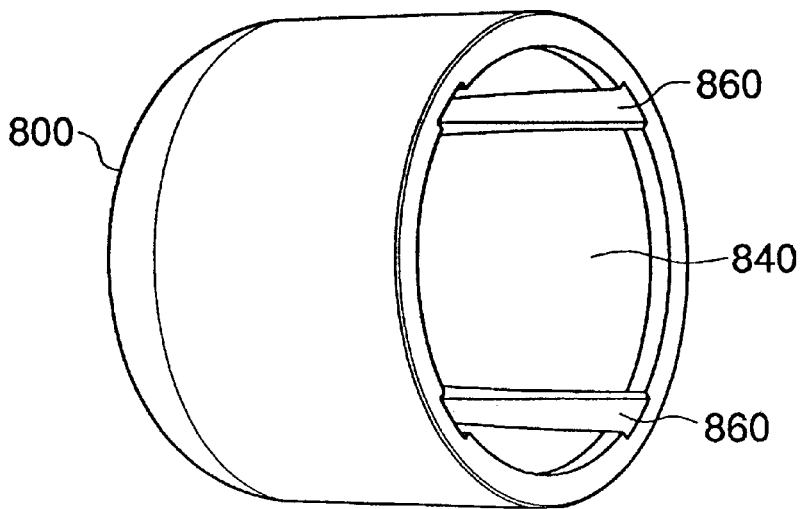
FIG. 25 is a perspective view of the safety cap of FIGS. 14a and 14b.
Figure 26:
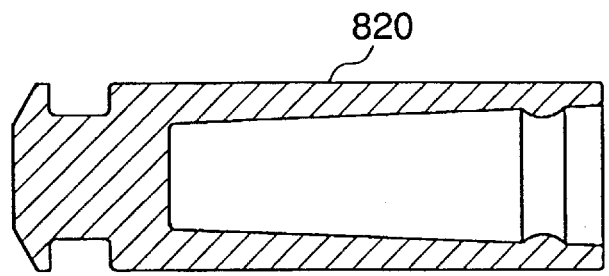
FIG. 26 is a cross-sectional view of the needle cap of FIGS. 14a and 14b.

The device also features a removable safety cap 800 that slides over the needle guard 540 and covers the device prior to its use. The safety cap 800 includes a needle cap 820 (FIG. 26) connected thereto, the needle cap 820 forming a sterile barrier around the needle assembly 460. As shown in FIG. 25, the safety cap 800 has four longitudinal recesses 860 equally displaced about its inner surface 840. These longitudinal recesses 860 are dimensioned to accept two or more bosses 880 located at corresponding locations on the needle guard 540. Because of these two features, clockwise rotation of the safety cap 800 causes corresponding rotation of the needle guard 540 and the needle holder 260. Thus, the user may turn the safety cap 800 clockwise one quarter turn, prior to removing it from the device, to create the drug path and prepare the device for injection.

The device of the preferred embodiment is operated by first turning the safety cap 800 clockwise one quarter of a turn, to create the drug path by inserting the proximal end of injecting needle 480 into the ampule 320. Rotating the safety cap 800 also aligns the cutaways 645 in the safety cap 560 with the bosses 625 on the inner housing 25, allowing the needle guard 540 to be depressed. Next the safety cap 800 and consequently the needle cap 820 are removed from the device.

Figure 28:
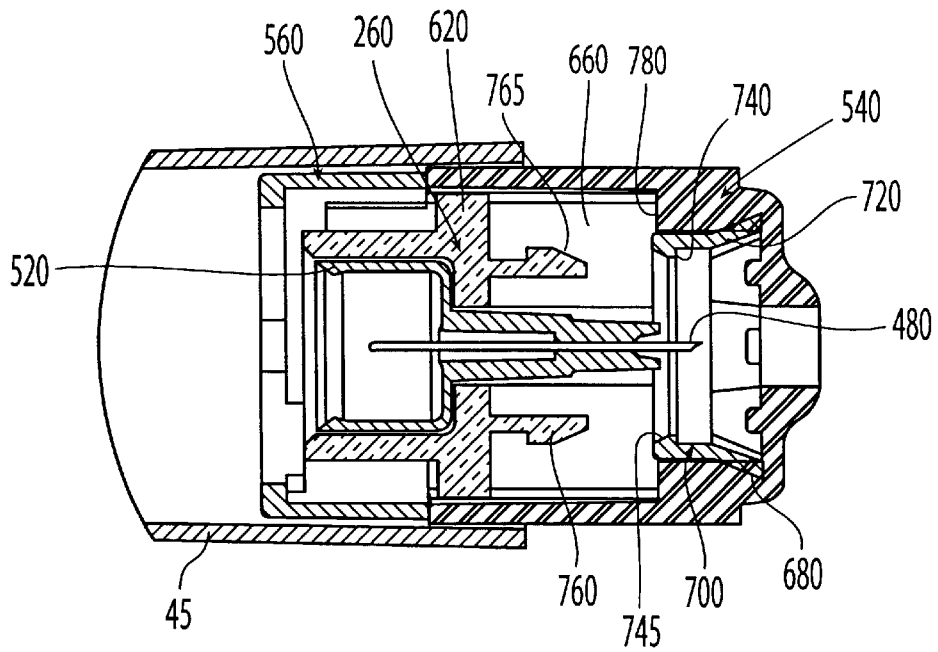
FIG. 28 is a partial cross-sectional view of another embodiment of the jet injector according to the invention with the safety cap removed, showing the injecting end of the injector with the needle in a retracted position prior to and ready for use with the needle guard fully extended.
Figure 29:
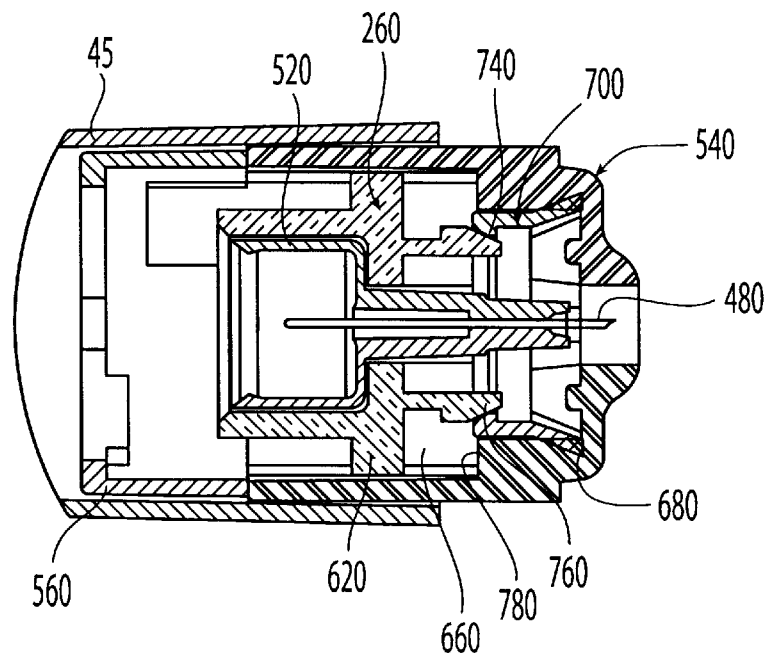
FIG. 29 is a cross-sectional view of the jet injector of FIG. 28 with the needle in a partially retracted position and the needle guard in an intermediate position as if partially pressed against an injecting surface prior to use, but not pressed in far enough to activate the injector.

Referring to FIGS. 28–31, the operation of the device is illustrated showing a series of positions for the injection process. Referring to FIG. 28, the device is shown in the latched and ready to fire position, but prior to being pressed against a user's skin. The needle guard 540 is shown fully extended and needle 480 is retracted inside the needle guard 540. In FIG. 29, the device is pressed against a user's skin and the needle guard 540 is partially retracted. The ramped portion 765 of the holder 260 and the ramp 745 of the locking ring 700 come into contact. The action of the two ramp portions sliding past one another generates a force greater than the return spring (not shown, but location referred to as location 660). As the user continues to press the needle guard 540 against the skin, the extensions 760 of the holder 260 are forced into the undercut 740 of locking ring 700. The force necessary to push the extensions 760 into under 740 is a threshold which must be overcome to fire the device. Once the extensions 760 are forced into the undercut 740 such that the threshold force has been overcome, holder 260 will slide rapidly forward into the locking ring, causing the injector to fire. As the distal end of the device is pressed against the injection site, the injecting needle 480 enters the skin to a depth of between 1 and 5. The movement of the needle guard 540 causes the ram 125 to fire and consequently between 0.02 and 2.0 of medicament 400 is forced out of the ampule 320 and through the drug path in under about 2.75 seconds.

Figure 30:
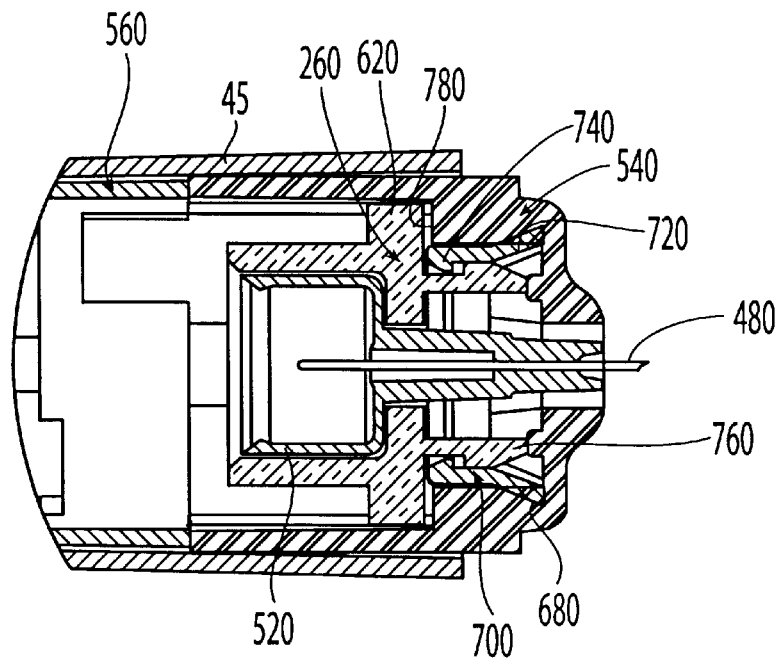
FIG. 30 is a cross-sectional view of the jet injector of FIG. 28 with the needle in an extended position and the injector has been fired for injection into a user.

As shown in FIG. 30, the needle 480 is fully extended such that it has entered the skin of a user and the injector has fired. The extensions 760 are forced into undercut 740. The engagement between extensions 760 and undercut 740 prevents holder 260 and locking ring 700 from separating.

Referring to FIG. 31, the needle guard 540 is shown after being removed from the injection site. Once the device is removed from the injection site, the needle guard 540 returns to its original position under the force of return spring 660, concealing the injecting needle 480. The legs 720 of locking ring 700 are withdrawn from the pocket 680 in needle guard 540 and are extended or sprung outwardly. In this position, legs 720 engage shoulder 780 of needle guard 540 if a user attempts to reuse the needle 480, thereby preventing reuse. In this way, the locking ring 700 locks the needle guard 540 in place to prevent re-exposure of the injecting needle 480. Alternatively, a push button could be located at the proximal end of the device and be locked in an idle position. The movement of the needle guard 540 could unlock the push button and allow the user to depress it and consequently fire the device.

Figure 20B:
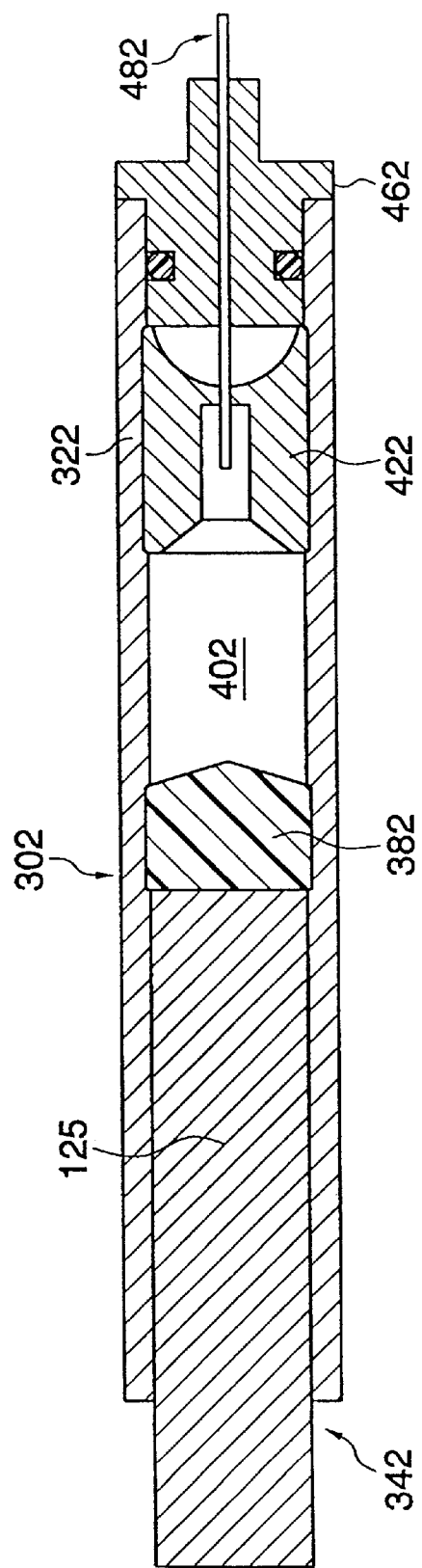
FIG. 20b is a cross-sectional view of an alternative embodiment of the cartridge assembly of FIGS. 14a and 14b.

FIG. 20b shows another embodiment of the cartridge assembly 302 of the preferred embodiment. The cartridge assembly 302 comprises a glass ampule 322 and a needle assembly 462 sealed on its distal end. A pierceable seal 422 is located in proximity to the proximal end of the injecting needle 482 and creates a barrier between the medicament 402 and the injecting needle 482. A rubber stopper 382 is slideable within the glass ampule 322 and seals an opening 342 in its proximal end so the medicament 402 stays inside the glass ampule 322. Upon firing of the injector, the ram 125 urges the rubber stopper 382 toward the distal end of the injector. Since the medicament 402 is an incompressible fluid, the pierceable seal 422 is forced onto the distal end of the injecting needle 482, thereby breaking the barrier and creating the drug path. With this cartridge assembly 302, no turning of the device is required to create the drug path, and the threads on the inner housing 25 and on the needle holder 260 can be replaced by known permanent fixing techniques, such as gluing or welding.

Figure 27:
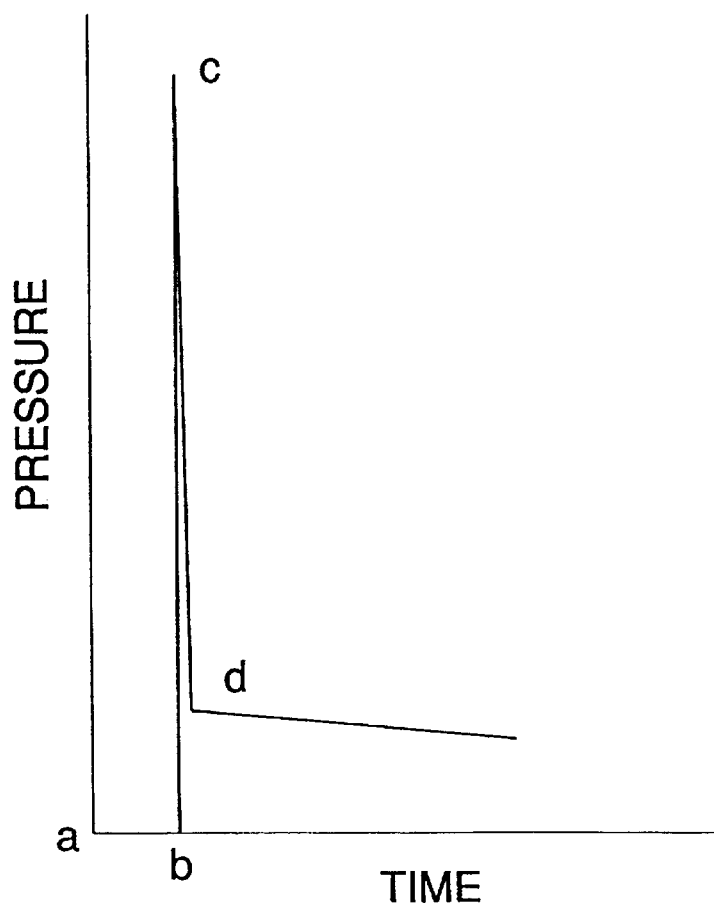
FIG. 27 is a schematic expressing a pressure-time curve for a jet injector.

A significant advantage of the needle assisted jet injector according to the present invention is that it allows for a lower pressure to deliver the medicament at the desired rate. In this regard, administering an injection using either a fixed or retractable needle requires less energy and force than conventional jet injector devices. FIG. 27 shows a pressure-time curve for a jet injector. The peak pressure at point c is the pressure needed to penetrate the skin and point d and beyond is the pressure at which a jet stream of medicament is delivered. As shown in the chart below, needle assisted jet injectors do not need to achieve as high as peak pressure as conventional jet injectors because the outer layer of skin is penetrated by the needle.

Pressure and Time (sec.) to Inject 1 cc

| Pressure | 26 Gauge needle | 27 Gauge needle |
| --- | --- | --- |
| 150 psi | 2.1 | 4.2 |
| 200 psi | 1.9 | 3.9 |
| 240 psi | 1.7 | 3.3 |
| 375 psi | 1.4 | 3.1 |

A lower peak pressure can be used to deliver the medicament to the desired region and still achieve a short injection time. It is also possible that a lower steady state pressure can be used to deliver the jet stream after the needle and the jet injection have reached the desired region.

Reduced operating pressure decreases the chances of glass ampule breakage. The chart below shows the statistical predictions of breakage for glass cartridges at different pressures, based on the Gausian distribution of actual breakage rates at various pressures.

Breakage Rates for Glass Cartridges

| Pressure (psi) | Breakage Rate |
| --- | --- |
| 310 | $1.5 \times 10^{-11}$ |
| 412 | $1.0 \times 10^{-9}$ |

It can be seen that a relatively small increase in pressure (≈100 p.s.i.) increases the breakage rate by two orders of magnitude. Thus, the reduced operating pressure of the needle assisted injection device of the present invention greatly reduces the risk of ampule breakage.

Experimentation has confirmed that the needle assisted injector according to the present invention can be operated using a lower generating energy source and still maintain the quality of the injection. Specifically, experimentation has shown that a higher percentage of successful injections can be achieved with a needle assisted jet injector having a needle that penetrates the skin to a depth of 1 mm and 20 lb. force generating means as with a conventional needleless jet injectors having 55 lb. force generating means. Similar results have been achieved with needles that penetrate 1–3 mm and force generating sources providing 20 lbs. and 40 lbs. of force.

Another advantage of the needle assisted jet injector according to the present invention, shown in the chart below, is the decreased injection time compared to syringes or auto-injectors.

Comparison of Operating Properties for Injection Devices

| | Spring Force (Lbf.) | Dia. Of Fluid Chamber (inches) | Avg. Pressure (psi) | Volume of Injection (ml) | Injection Time (sec) |
| --- | --- | --- | --- | --- | --- |
| Jet Injector | 110 | 0.233 | 2111 | 0.5 | 0.165 |
| 1st Needle Assisted Injector | 30 | 0.352 | 227 | 0.5 | <1 |
| 2nd Needle Assisted Injector | 15 | 0.231 | 233 | 0.5 | <1 |
| Conventional Syringe | N/A | 0.351 | 5 | 0.5 | 3–5 |

As previously discussed, auto-injectors and syringes have injection times of several seconds or more. During this injection time, the quality of the injection can be compromised due to any number of factors. For example, the patient could move the syringe or auto-injector prior to completion of the injection. Such movement could occur either accidently or intentionally because of injection-related pain. In contrast, the needle assisted jet injector, like other jet injectors, can have an injection time of less than 1 second. The short injection time minimizes the possibility of compromising the quality of the injection.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A locking mechanism for use with a needle assisted jet injector, the needle assisted jet injector having a needle assembly with a needle and a needle guard associated with the needle assembly, said needle guard for placement against a surface to be injected and for guarding the needle before and after an injection of the injector, the needle guard being movable between a first retracted position wherein the needle is retracted inside the needle guard, an extended position wherein the needle extends outside the needle guard for injection into the surface, and a second retracted position wherein the needle is retracted inside the needle guard after injection, said locking mechanism comprising:

a holder member adapted for holding a needle assembly and having at least one first engaging portion; and locking means operatively associated with a needle guard and the holder member for engagement with at least one first engaging portion of the holder member in the extended and second retracted positions;

wherein the locking means is associated with a needle guard in the first retracted position, is associated with the holder member in the extended and second position and is in blocking relation with a needle guard into the extended position and deter reuse of a needle; and wherein the holder member includes:

a substantially cylindrical portion at a proximal end thereof;

at least one first engaging portion at a distal end thereof; and an inner wall positioned substantially therebetween, said cylindrical portion and inner wall being configured and dimensioned for mating with a needle assembly.

2. The locking mechanism of claim 1, wherein the inner wall includes a circular opening extending between the proximal and distal sides thereof for receiving a portion of a needle assembly therethrough.

3. The locking mechanism of claim 1 wherein the locking means has at least one second engaging portion which is configured and dimensioned with respect to the first engaging portion of the holder member for releasable mating engagement therewith.

4. A locking mechanism for use with a needle assisted jet injector, the needle assisted jet injector having a needle assembly with a needle and a needle guard associated with the needle assembly, said needle guard for placement against a surface to be injected and for guarding the needle before and after an injection of the injector, the needle guard being movable between a first retracted position wherein the needle is retracted inside the needle guard, an extended position wherein the needle extends outside the needle guard for injection into the surface, and a second retracted position wherein the needle is retracted inside the needle guard after injection, said locking mechanism comprising:
  a holder member adapted for holding a needle assembly and having at least one first engaging portion; and
  a locking member operatively associated with a needle guard and the holder member, said locking member having at least one second engaging portion for engagement with the at least one first engaging portion of the holder member in the extended and second retracted positions,
  wherein the locking member is associated with a needle guard in the first retracted position, is associated with the holder member in the extended and second retracted positions, and is in blocking relation with a needle guard in the second retracted position so as to block further movement of a needle guard into the extended position and deter reuse of a needle; and
  wherein the holder member includes:
    a substantially cylindrical portion at a proximal end thereof;
    the at least one first engaging portion is at least one arm extending distally from an inner wall, said arm including an extension portion configured and dimensioned for seating in the second engaging portion of the locking member; and
    the inner wall positioned substantially therebetween, said cylindrical portion and inner wall being configured and dimensioned for mating with a needle assembly.

5. The locking member of claim 4, wherein the extension portion of the arm of said first engaging portion includes a ramped portion for association with the locking member.

6. A needle assisted jet injector, comprising
  a needle assembly with a needle; and
  a needle guard associated with the needle assembly, said needle guard for placement against a surface to be injected and for guarding the needle before and after an injection of the injector, the needle guard being movable between a first retracted position wherein the needle is retracted inside the needle guard, an extended position wherein the needle extends outside the needle guard for injection into the surface, and a second retracted position wherein the needle is retracted inside the needle guard after injection; and
  a locking mechanism comprising:
    a holding member configured and dimensioned to hold the needle assembly and having at least one first engaging portion; and
    locking means operatively associated with the needle guard and the holder member for engagement with the at least one first engaging portion of the holder in the extended and second retracted positions,
    wherein the locking means is associated with the needle guard in the first retracted position, is associated with the holder member in the extended and second retracted positions, and is in blocking relation with the needle guard in the second retracted position so as to block further movement of the needle guard into the extended position and deter reuse of the needle.

7. The needle assisted jet injector of claim 6, wherein the holder member includes:
  a substantially cylindrical portion at a proximal end thereof;
  the at least one first engaging portion at a distal end thereof; and
  and an inner wall positioned substantially therebetween, said cylindrical portion and inner wall being configured and dimensioned for mating with the needle assembly.

8. The needle assisted jet injector of claim 6, wherein the locking means has at least one second engaging portion which is configured and dimensioned with respect to the first engaging portion of the holder member for releasable mating engagement therewith.

9. A needle assisted jet injector, comprising:
  a needle assembly with a needle; and
  a needle guard associated with the needle assembly, said needle guard for placement against a surface to be injected and for guarding the needle before and after an injection of the injector, the needle guard being movable between a first retracted position wherein the needle is retracted inside the needle guard, an extended position wherein the needle extends outside the needle guard for injection into the surface, and a second retracted position wherein the needle is retracted inside the needle guard after injection; and
  a locking mechanism comprising:
    a holder member configured and dimensioned to hold the needle assembly and having at least one first engaging portion; and
    a locking member operatively associated with the needle guard and the holder member, said locking member having at least one second engaging portion for engagement with the at least one first engaging portion of the holder member in the extended and second retracted positions,
  wherein the locking member is associated with the needle guard in the first retracted position, is associated with the holder member in the extended and second retracted positions, and is in blocking relation with the needle guard in the second retracted position so as to block further movement of the needle guard into the extended position and deter reuse of the needle; and
  wherein the locking member includes:
  a substantially annular portion;
  at least one outwardly-biased leg extending from a distal end of said annular portion; and
  the needle guard includes at least one pocket for accepting the at least one leg when the locking member is associated with the needle guard in the first retracted position, wherein the leg maintains its position in association with the needle guard due to its outwardly-biased force, said leg being resilient such that it is removable from the at least one needle guard pocket upon the application of sufficient force to overcome the outwardly-biased force of said leg.

10. The needle assisted jet injector of claim 9, wherein the locking member has an undercut portion formed at a proximal end of the annular portion, said undercut portion being dimensioned and configured to accept the first engaging portion of the holder member for mating therewith.

11. The needle assisted jet injector of claim 10, wherein the proximal end of the annular portion further comprises a ramp portion on an inner surface extending inwardly from the end thereof, said locking member ramp portion being angled relative to an outer circumferential surface of the annular portion for engagement with the first engaging portion of the holder member before the holder member engages the undercut.

12. The needle assisted jet injector of claim 11, wherein the holder member includes:
   a substantially cylindrical portion at a proximal end thereof;
   the at least one first engaging portion at a distal end thereof; and
   and an inner wall positioned substantially therebetween, said cylindrical portion and inner wall being configured and dimensioned for mating with a needle assembly,
   wherein the first engaging portion is at least one arm extending distally from the inner wall, said arm including an extension portion configured and dimensioned for seating in the second engaging portion of the locking member, said extension portion of the arm including a ramped portion for association with the ramped portion of the locking member.

13. The needle assisted jet injector of claim 12, wherein the ramped portion of the holder member is complementary to the ramped portion of the locking member such that both ramped portions allow the other ramped portion to slide thereupon allowing the first engaging portion to engage the second engaging portion in the extended position.

14. The needle assisted jet injector of claim 9, wherein the at least one outwardly-biased leg springs outwardly after disengagement with a needle guard pocket and abuts a shoulder formed on an inner surface of a needle guard in the second retracted position to prevent reuse of a needle by substantially blocking proximal movement of a needle guard.

15. The needle assisted jet injector of claim 9, wherein the at least one second engaging portion of the locking member is an undercut portion formed at a proximal end of the annular portion, said undercut portion being dimensioned and configured to accept the first engaging portion of the holder member for mating therewith;
   the proximal end of the annular portion further comprises a ramp portion on an inner surface extending inwardly from the end thereof, said locking member ramp portion being angled relative to an outer circumferential surface of the annular portion for engagement with the first engaging portion of the holder member before the holder member engages the undercut; and
   the at least one outwardly-biased leg springs outwardly after disengagement with the at least one needle guard pocket and abuts a shoulder formed on an inner surface of the needle guard in the second retracted position to prevent reuse of the needle by substantially blocking proximal movement of the needle guard.

16. The needle assisted jet injector of claim 9, wherein the holder member includes:
   a substantially cylindrical portion at a proximal end thereof;
   the at least one first engaging portion at a distal end thereof; and
   and an inner wall positioned substantially therebetween, said cylindrical portion and inner wall being configured and dimensioned for mating with the needle assembly.

17. The needle assisted jet injector of claim 16, wherein the first engaging portion is at least one arm extending distally from the inner wall, said arm including an extension portion configured and dimensioned for seating in the second engaging portion of the locking member, said extension portion of the arm including a ramped portion for association with the ramped portion of the locking member.

18. The needle assisted jet injector of claim 17, wherein the ramped portion of the holder member is complementary to the ramped portion of the locking member such that both ramped portions allow the other ramped portion to slide thereupon allowing the first engaging portion to engage the second engaging portion in the extended position.

19. The needle assisted jet injector of claim 16, wherein the inner wall includes a circular opening extending between the proximal and distal sides thereof for receiving a portion of the needle assembly therethrough.

20. A needle assisted jet injector, comprising
   a needle assembly with a needle; and
   a needle guard associated with the needle assembly, said needle guard for placement against a surface to be injected and for guarding the needle before and after an injection of the injector, the needle guard being movable between a first retracted position wherein the needle is retracted inside the needle guard, an extended position wherein the needle extends outside the needle guard for injection into the surface, and a second retracted position wherein the needle is retracted inside the needle guard after injection; and
   a locking mechanism comprising:
      a holding member configured and dimensioned to hold the needle assembly and having at least one first engaging portion;
   wherein the holder member includes:
      a substantially cylindrical portion at a proximal end thereof;
      the at least one first engaging portion at a distal end thereof; and
   an inner wall positioned substantially therebetween, said cylindrical portion and inner wall positioned substantially therebetween, said cylindrical portion and inner wall being configured and dimensioned for mating with the needle assembly; and
   a locking member operatively associated with the needle guard and the holder member, said locking member having at least one second engaging portion for engagement with the at least one first engaging portion of the holder in the extended and second retracted positions,
   wherein the locking member is associated with the needle guard in the first retracted position, is associated with the holder member in the extended and second retracted positions, and is blocking relation with the needle guard in the second retracted position so as to block further movement of the needle guard into the extended position and deter reuse of the needle; and
   wherein the first engaging portion is at least one arm extending distally from the inner wall, said arm including an extension portion configured and dimensioned for seating in the second engaging portion of the locking member, said extension portion of the arm including a ramped portion for association with the ramped of the locking member, said extension portion of the arm including a ramped portion for association with the ramped portion of the locking member.

21. An injection device comprising:

a housing having a distal end and a proximal end;

a fluid chamber located within said housing for holding a fluid;

a needle assembly associated with the fluid chamber and having an injection-assisting needle, said needle assembly positioned at the distal end of the housing for delivering fluid from the fluid chamber;

a plunger movable within the fluid chamber;

a force generating source for generating sufficient force on the plunger to eject fluid from the fluid chamber through the needle;

a needle guard positioned at the distal end of the housing for concealing the needle, the needle guard being movable between a first retracted position wherein the needle is retracted within the needle guard before injection, an extended position wherein the needle is extended outside the needle guard for injection, and a second retracted position wherein the needle is retracted inside the needle guard after injection, an activation element operatively associated with the needle guard such that movement of the needle guard to the extended position activates the force generating source; and a locking mechanism operatively associated with the needle guard and the needle assembly, said locking mechanism including:

a holder member configured and dimensioned to hold the needle assembly and having a first engaging portion; and a locking member operatively associated with the needle guard and the holder member, said locking member having at least one second engaging portion for engagement with the first engaging portion of the holder member in the extended and second retracted positions, wherein the locking member is associated with the needle guard in the first retracted position, is associated with the holder member in the extended and second retracted positions, and is in blocking relation with the needle guard in the second retracted position, said locking member being configured and dimensioned to block further movement of the needle guard in the second retracted position to deter reuse of the needle and substantially block further movement of the needle guard toward the extended position.

* * * * *

UNITED STATES PATENT AND TRADEMARK OFFICE
CERTIFICATE OF CORRECTION

PATENT NO.   : 6,391,003 B1
DATED        : May 21, 2002
INVENTOR(S)  : Lesch, Jr.

It is certified that error appears in the above-identified patent and that said Letters Patent is hereby corrected as shown below:

Column 14,
Line 65, before "at least one first engaging portion at a distal end thereof;", insert -- the --.

Column 18,
Line 62, after "positions, and is", insert -- in --.

Column 19,
Lines 5-7, delete "of the locking member, said extension portion of the arm including a ramped portion for association with the ramped".

Signed and Sealed this

Tenth Day of September, 2002

Attest:

Attesting Officer

JAMES E. ROGAN
Director of the United States Patent and Trademark Office